(12) United States Patent
Sell

(10) Patent No.: US 6,783,942 B2
(45) Date of Patent: Aug. 31, 2004

(54) ISOLATED POLYNUCLEOTIDE ASSOCIATED WITH TYPE II DIABETES MELLITUS AND METHODS OF USE THEREOF

(75) Inventor: Susan M. Sell, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/012,282

(22) Filed: Nov. 5, 2001

(65) Prior Publication Data

US 2002/0137079 A1 Sep. 26, 2002

Related U.S. Application Data

(63) Continuation-in-part of application No. 09/415,482, filed on Oct. 8, 1999, now abandoned.
(60) Provisional application No. 60/103,680, filed on Oct. 8, 1998.

(51) Int. Cl.$^7$ .......................... C07H 21/04; C12Q 1/68
(52) U.S. Cl. ........................ 435/6; 435/91.1; 435/91.2; 536/23.1
(58) Field of Search .......................... 435/6, 91.1, 91.2; 536/23.1

(56) References Cited

U.S. PATENT DOCUMENTS 5,474,796 A 12/1995 Brennan

OTHER PUBLICATIONS

Permutt et al. "Searching for Type 2 diabetes genes on chromosome 20." Diabetes. vol. 51, Suppl. 3, pp. S308–315, Dec. 2002.*
Genethon– Chromosome 20. Nature Genetics. vol. 7, pp. 328–331, Jun. 1994.*
Bowden et al. "Linkage of geneti markers on human chromosomes 20 and 12 to NIDDM in Caucasian sib pairs with a hisotry of dibetic nephropathy". Diabetes. vol. 46, pp. 882–886, May 1997.*
Ji et al. "New Susceptibility locus for NIDDM is localized to Human chromosome 20q." Diabetes. vol. 46, pp. 876–881, May 1997.*
Genbank Accession No. Z16656. Weissenbach et al. "*H. sapiens* (D20S107) DNA segment containing (CA) repeat" Nov. 28, 1994.*
Altshuler et al. "The common PPARPro12Ala polymorphism is associated with decreased risk of type 2 diabetes." Nature Genetics, vol. 26, pp. 76–80, Sep. 2000.*
Kim et al. (2000) J. Biol. Chem. 275:8456–60.
Venter et al. (2001) *Science* 1304.
Wang et al. (1999) *Genomics* 59:275–281.
Taylor, ed. (1997), "Laboratory Methods for the Detection of mutations and Polymorphisms," CRC Press.

Bell et al. (Feb. 1991), "Gene for Non–Insulin–Dependent Diabetes Mellitus (Maturity–Onset Diabetes of the Young Subtype) is Linked to DNA Polymorphism on Human Chromosome 20q." *Proc. Natl. Acad. Sci. USA*, vol. 88:1484–1488.
Chèvre et al. (1998), "Mutation Screening is 18 Caucasian Families Suggest the Existence of Other MODY Genes," *Diabetologia*, vol. 41 :1017–1023.
Altman et al. (Jul. 1995), "Molecular genetics of Diabetes Mellitus," *Bailliers Clin. Endocrinology & Metabolism*, vol. 9(3):631–56.
Barnett et al. (1981), "Diabetes in Identical Twins– A Study of 200 Pairs," *Diabetologia*, vol. 20:87–93.
Barnett et al. (May 23, 1981)," Metabolic Studies in Unaffected Co–Twins of Non–Insulin–Dependent Diabetics," *Brit. Med. J.*, vol. 282:1656–1658.
Björntorp (1992), "Regional Obesity," *Obesity*, 579–586.
Bowden et al. (May 1997)."Linkage of Genetic Markers on Human Chromosomes 20 and 12 to NIDDM in Caucasian Sib Pairs with a History of Diabetic Nephropathy," *Diabetes*, vol. 45(5):882–86.
Chadwick et al: (Apr. 1996), "Heterozygole and Mutation Detection by Direct Automated Fluorescent Sequencing Using a Mutant Taq DNA Polymerase," *Biotechniques*, vol. 20:676–683.
Cook et al. (1994), "Segregation Analysis of NIDDM in Caucasian Families," *Diabetologia*, vol. 37(12):1231–40.
Deuter et al. (1998), "Detection of APC Mutations in Stool DNA of Patients with Colorectal Cancer by HD–PCR," *Human Mutat.*, vol. 11:84–89.
Elston et al. (1974), "Studies on Blood and Urine Glucose in Seminole Indians: Indications for Segregation of a Major Gene," *Amer. J. of Human Genetics*, vol. 26(1):13–34.
Freimer et al. (1996), "An Approach to Investigating Linkage for Bipolar Disorder Using Large Cosat Rican Pedigrees," *Am. J. of Medical Genetics (Neuropsychiatric Genetics)*, vol. 67:254–263.
Hanl et al. (1998), "A Missense Mutation in Hepatocyte Nuclear Factor–4α, Resulting in a Reduced Transactivation Activity, in Human Late–onset Non–Insulin–Dependent Diabetes Mellitus," *J. Clin. Invest.*, vol. 101:521–526.

(List continued on next page.)

Primary Examiner—Jeffrey Fredman
Assistant Examiner—Jeanine Goldberg
(74) *Attorney, Agent, or Firm*—Paula A. Borden; Bozicevic, Field & Francis, LLP

(57) ABSTRACT

The present invention provides isolated polynucleotides that include sequences from a region of human chromosome 20q between D20S119 and D20S195. The polynucleotides include polymorphisms associated with Type II diabetes and are useful as probes in screening for Type II diabetes. The invention further provides vectors and isolated host cells comprising the isolated polynucleotides. The invention further provides methods of detecting polymorphisms on chromosome 20q between D20S119 and D20S195, and methods of detecting a propensity to develop Type II diabetes, using the isolated polynucleotides of the invention.

5 Claims, 6 Drawing Sheets

OTHER PUBLICATIONS

Hanis et al. (Jun. 1996), "A Genome–wide Search for Human Non–Insulin–Dependent (Type 2) Diabetes Genes Reveals a Major Susceptibility Locus on Chromosome 2," *Nature Genetics*, vol. 13:161–6.

Hanson et al. (1995), "Segregation Analysis of Non–Insulin–Dependent Diabetes Mellitus in Pima Indians: Evidence for a Major–Gene Effect," *Amer. J. of Human Genetics*, vol. 57(1):160–170.

Hanson (May 1997), "Genomic Scan for Makers Linked to Type II Diabetes in Pima Indians," *Diabetes–Abstract Book 57th Annual Meeting and Scientific Sessions*, vol. 46:S1:51A.

Häsbacka et al. (Nov. 1992), "Linkage Disequilibrium Mapping in Isolated Founder Populations: Diastrophic Dysplasia in Finland," *Nature Genetics*, vol. 2:204–211.

Hästbacka et al. (Sep. 23, 1994), "The Diastrophic Dysplasia Gene Encodes a Novel Sulfate Transporter. Positional Cloning by Fine–Structure Linkage Disequillibrium Mapping," *Cell*, vol. 78:1073–1087.

Healy et al. (1997), "Fiberoptic DNA Sensor Array Capable of Detecting Point Mutations," *Anal. Biochem.*, vol. 251:270–279.

Ji et al. (May 1997), "New Susceptibility Locus for NIDDM is Localized to Human Chromosome 20q," *Diabetes*, vol. 46:876–81.

Jorde (1995), "Invited Editorial–Linkage Disequilibrium as a Gene–Mapping Tool," *Amer J. of Human Genetics*, vol. 56(1):11–14.

Kahn et al. (1996), "Genetics of Non–Insulin–Dependent (Type–II) Diabetes Mellitus," *Ann. Rev. of Med.*, vol. 47:509–31.

Kekes–Szabo et al. (1996), "Anthropometric Equations for Estimating Abdominal Adipose Tissue Distribution In Women," *Intl. J. of Obesity & Related Metabolic Disorders*, vol. 20(8):753–8.

Kekes–Szabo et al. (Sep. 1994), "Development and Validation of Computed Tomography Derived Anthropometric Regression Equations for Estimating Abdominal Adipose Tissue Distribution," *Obesity Res.*, vol. 2(5):450–457.

Kerem et al. (Sep. 8, 1989), "Identification of the Cystic Fibrosis Gene: Genetic Analysis," *Science*, vol. 245:1073–1080.

Kissebah et al. (1982), "Relation of Body Fat Distribution to Metabolic Complications of Obesity," *J. of Clinical Endocrinology & Metabolism*, vol. 54(2):254–60.

Knowler, W.C et al. (1988), "Genetic and Environmental Factors in the Development of Diabetes Mellitus in Pima Indinans," *Genetic Suspectability to Environmental Factors.A Challenge for Public Intervention*, Almquist and Wiksele International: Stokholm, p. 67–74.

Lander et al. (Oct. 1986), "Strategies for Studying Heterogeneous Genetic Traits in Humans by Using a Linkage Map of Restriction Fragment Length Polymorphisms," *Proc. Natl. Acad. Sci. USA*, vol. 83:7353–7357.

Mahtani et al. (Sep. 1996), "Mapping of a Gene for type 2 Diabetes Associated with an Insulin Secretion Defect by a Genome Scan in Finnish Families," *Nature Genetics*, vol. 14:90–4.

Marshall et al. (Jan. 1998), "DNA Chips: An Array of Possibilities," *Nature Biotechnology*, vol. 16:27–31.

McCarthy et al. (1994), "Family Studies of Non–Insulin–Dependent Diabetes Mellitus in South Indians," *Diabetologia*, vol. 37(12):1221–30.

Risch et al. (Sep. 13, 1996), "The Future of Genetic Studies of Complex Human Diseases," *Science*, vol. 273:1516–1517.

Serjeantson et al. (Sep. 1991), "Genetics of Non–Insulin Dependent Diabetes Mellitus in 1990," *Baillieres Clin. Endocrinology & Metabolism*, vol. 5(3):477–93.

Service, et al. (1997) *J. of Human Genetics*, vol. 159:A236.

Spielman et al.(1993), "Transmission Test for Linkage Disequilibrium: The Insulin Gene Region and Insulin–Dependent Diabetes Mellitus (IDDM)," *Am. J. of Human Genet.*, vol. 52:506–516.

Terwilliger (1995), "A Powerful Likelihood Method for the Analysis of Linkage Disequilibrium between Trait Loci and One or More Polymorphic Marker Loci," *Am. J. Hum. Genet.*, vol. 56:777–787.

Vague et al. (1996), "Sexual Differentiation. A Determinant Factor of the Forms of Obesity," *Obesity Research*, vol. 4(2):201–203.

Vaughan et al. (1998), "A Novel Process for Mutation Detection Using Uracil DNA–Glycosylase," *Nucl. Acids Res.*, vol. 26(3):810–815.

Velho et al. (1997), "Maturity–Onset Diabetes of the young (MODY), MODY Genes and Non–Insulin–Dependent Diabetes Mellitus," *Diabetes and Metabolism*, vol. 23 (Suppl 2):34–37.

Velho et al. (1998), "Genetic, Metabolic and Clinical Characteristics of Maturity Onset Diabetes of the Young," *Eur. J, Endocrinology*, vol. 138:233–239.

Weber et al. (1993), "Evidence of Human Meiotic Recombination Interference Obtained through Construction of a Short Tandem Repeat–Polymorphism Linkage Map of Chromosome 19," *Am. J. of Human Genetics*, vol. 53:1079–1095.

Weissenbach et al. (Oct. 29, 1992), "A Second–Generation Linkage Map of the Human Genome," *Nature*, vol. 359:794–801.

Wong et al. (1997), "Direct Detection of Multiple Point Mutations in Mitochondrial DNA," *Clin. Chem.*, vol. 43(10):1857–1861.

Yamagata et al. (1996), "Mutations in the Hepatocyte Nuclear Factor–4α Gene in Maturity–Onset Diabetes of the Young (MODY1)," *Nature*, vol. 384:458–460.

Zouall et al. (1997), "A Susceptibility Locus for Early–Onset Non–Insulin Dependent (Type 2) Diabetes Mellitus Maps to Chromosome 20q, Proximal to the Phosphoenolpyruvate Carboxykinase Gene," *Human Molec. Genet.*, vol. 6(9):1401–1408.

Chromosome 20 Summary Map– http://cedar.genetics.soton.ac.uk/pub/chrom20/map.html.

* cited by examiner

SEQ ID NO:7
5'-
GTTTTCTTGGCTTTAGTCCTTAAAAATAAATCAAAACTGATTTAGAGAATGTT
TGGGCTTATCAGAAAGTCATT(A/T)TCCCCTGGCTGTCCTTAGCAAGACCTCAC
AGCATCACAGTGAAACAAAGTATGCTAAATTGAACAAACAGATGGACATGG
GCCCTATGCCCGGAATCACCGGAGACCCTTAAGGAACCCCTTTGGTGGAAGA
GCTGCACCAGTGTTGGGCTGAGGAGTCAGCAGACCTGGATTTGAGTCTGGAC
TCCAATACTGTGCAACCCTGG(A/G)TAAGTTACTTAACCTCTCTGAGTCTCAG
CTTCCTTTTCTCCACTTTGAGTAATGGTCTC-3'

FIGURE 5B

SEQ ID NO:8
5'-
GTTTTCTTGGCTTTAGTCCTTAAAAATAAATCAAAACTGATTTAGAGAATGTT
TGGGCTTATCAGAAAGTCATT(A/T)TCCCCTGGCTGTCCTTAGCAAGACCTCAC
AGCATCACAGTGAAACAAAGTATGCTAAATTGAACAAACAGATGGACATGG
GCCCTATGCCCGGAATCACCGGAGACCCTTAAGGAACCCCTTTGGTGGAAGA
GCTGCACCAGTGTTGGGCTGAGGAGTCAGCAGACCTGGATTTGAGTCTGGAC
TCCAATACTGTGCAATCCTGG(A/G)TAAGTTACTTAACCTCTCTGAGTCTCAGC
TTCCTTTTCTCCACTTTGAGTAATGGTCTC-3'

SEQUENCE LISTING

<160> NUMBER OF SEQ ID NOS: 12

<210> SEQ ID NO 1
<211> LENGTH: 369
<212> TYPE: DNA
<213> ORGANISM: Homo sapiens
<220> FEATURE:
<221> NAME/KEY: misc_feature
<222> LOCATION: (1)...(369)
<223> OTHER INFORMATION: n = A,T,C or G

<400> SEQUENCE: 1

```
agctctattt naggacaact cactcaatga tgttnttcag gccaggaatc actgacgtca      60
cttttccaag cagtccccca aggaggccac cagaagtacc tcctccaggc ttcaggatgt     120
ccaggagcgg aaggtttcc agaatgccca acaggccccc agacagcagg ccattgctga     180
gggctggaaa tgggtgtaag ggtctctggg ggtcagatct gacaattcca gatcctcagg     240 cccctcccc catccagccc tgtccctccc cactttgcag ggttggacac acacacacac     300
acacacacac acacacacac acacanat gcacacatac acccctgaaa antcaccatt     360 tgtnaagct                                                            369
```

<210> SEQ ID NO 2
<211> LENGTH: 320
<212> TYPE: DNA
<213> ORGANISM: Homo sapiens
<220> FEATURE:
<221> NAME/KEY: misc_feature
<222> LOCATION: (1)...(320)
<223> OTHER INFORMATION: n = A,T,C or G

<400> SEQUENCE: 2
agctaactga cacagtttca gtatctctat ctcacataaa cataaacata aacataaaca      60
tacacacaca cacacacaca cacacacacg cataaacata caccccctaaa tctggaaaaa    120 agagttctat tctttggaaa cttaggttca aatttaacta acattcacta aataccttct    180
acatttcagg ctttctacta ggtgctttca cataatggtc tcatccaaac tgcacatcca    240
aactgcatga ccaccatata aagtagaggg ggaaaagcct tacacttaat aggcatctnt    300
caagtgccag aaaatgtact                                                 320

<210> SEQ ID NO 3
<211> LENGTH: 332
<212> TYPE: DNA
<213> ORGANISM: Homo sapiens
<220> FEATURE:
<221> NAME/KEY: misc_feature
<222> LOCATION: (1)...(332)
<223> OTHER INFORMATION: n = A,T,C or G

<400> SEQUENCE: 3
agctccaaag gtttagtcta catgatgcct cttgggaatc cttctctgga gaagacattt      60
caaaacaaat ccaagccatc ttgttagagg ctaccctggg agagacaaag gtcaagaaat    120
aaaggttccc atgtgtctgg gtgcctattt agggcctcgc ctcgtcacac acacacacac    180
acacacacac acacacacac acacacacac ttgaggagtt atgacttaca actattctta    240
ttagaagaaa aacaggnttt ggagttgagg aatttgccat tgtctgaaac ttatttgagt    300
agtaactcag atggttctaa caaaatctag ct                                  332

<210> SEQ ID NO 4
<211> LENGTH: 329
<212> TYPE: DNA
<213> ORGANISM: Homo sapiens
<220> FEATURE:
<221> NAME/KEY: misc_feature
<222> LOCATION: (1)...(329)
<223> OTHER INFORMATION: n = A,T,C or G

<400> SEQUENCE: 4 cccttttaatg gattcttact gctctttcaa aaaagaaaaa aatctttttct naggctcctg    60 gccactgtcc atagcattca agtataccan tcttcctctt gctgtctgta ctgctgctaa   120
actgtctttc tgtttcttaa accccaaaca attcctctcc cttccttctt cccaagacac   180
acacacacac acacacacac acacacacac acacacacac tgattcccctt cacgtgtgnt   240 cttccttcat gtctttgctc atcagtccct tcactcatgg aagccccctc ttatacactc   300
ttagaatact ctattttta ctctgagct                                       329

<210> SEQ ID NO 5
<211> LENGTH: 19
<212> TYPE: DNA
<213> ORGANISM: Artificial Sequence
<220> FEATURE:
<223> OTHER INFORMATION: synthetic primer

```
<400> SEQUENCE: 5
gttttcttgg ctttagtcc                                              19

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
gagaccatta ctcaaagtgg                                             20

<210> SEQ ID NO 7
<211> LENGTH: 340
<212> TYPE: DNA
<213> ORGANISM: Homo sapiens

<400> SEQUENCE: 7
gttttcttgg ctttagtcct taaaaataaa tcaaaactga tttagagaat gtttgggctt   60
atcagaaagt cattwtcccc tggctgtcct tagcaagacc tcacagcatc acagtgaaac  120
aaagtatgct aaattgaaca aacagatgga catgggccct atgcccggaa tcaccggaga  180
cccttaagga accccttttgg tggaagagct gcaccagtgt tgggctgagg agtcagcaga 240
cctggatttg agtctggact ccaatactgt gcaaccctgg rtaagttact taacctctct  300
gagtctcagc ttcctttttct ccactttgag taatggtctc                       340

<210> SEQ ID NO 8
<211> LENGTH: 340
<212> TYPE: DNA
<213> ORGANISM: Homo sapiens

<400> SEQUENCE: 8
gttttcttgg ctttagtcct taaaaataaa tcaaaactga tttagagaat gtttgggctt   60
atcagaaagt cattwtcccc tggctgtcct tagcaagacc tcacagcatc acagtgaaac  120
aaagtatgct aaattgaaca aacagatgga catgggccct atgcccggaa tcaccggaga  180
cccttaagga accccttttgg tggaagagct gcaccagtgt tgggctgagg agtcagcaga 240
cctggatttg agtctggact ccaatactgt gcaatcctgg rtaagttact taacctctct  300
gagtctcagc ttcctttttct ccactttgag taatggtctc                       340

<210> SEQ ID NO 9
<211> LENGTH: 21
<212> TYPE: DNA
<213> ORGANISM: Artificial Sequence
<220> FEATURE:
<223> OTHER INFORMATION: synthetic primer

<400> SEQUENCE: 9
agctaactga cacagtttca g                                            21

<210> SEQ ID NO 10
<211> LENGTH: 21
<212> TYPE: DNA
<213> ORGANISM: Artificial Sequence
<220> FEATURE:
<223> OTHER INFORMATION: synthetic primer

<400> SEQUENCE: 10
agtacatttt ctggcacttg a                                            21
```

```
<210> SEQ ID NO 11
<211> LENGTH: 21
<212> TYPE: DNA
<213> ORGANISM: Artificial Sequence
<220> FEATURE:
<223> OTHER INFORMATION: synthetic primer

<400> SEQUENCE: 11
gcacacatac acccctgaaa a                                              21

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
tgaaactgtg tcagttagct                                                20
```

ISOLATED POLYNUCLEOTIDE ASSOCIATED WITH TYPE II DIABETES MELLITUS AND METHODS OF USE THEREOF

CROSS-REFERENCE

This application is a continuation-in-part application of Ser. No. 09/415,482, filed Oct. 8, 1999, now abandoned which claims the benefit of U.S. Provisional Patent Application Serial No. 60/103,680, filed Oct. 8, 1998, both of which are incorporated herein by reference in their entirety and to which applications priority is claimed.

FIELD OF THE INVENTION

The present invention is in the field of Type II diabetes, and in particular to genetic polymorphisms associated with Type II diabetes.

BACKGROUND OF THE INVENTION

Diabetes mellitus is a syndrome which results in disregulation of glucose homeostasis with multiple etiologic factors that generally involve absolute or relative insulin deficiency or insulin resistance or both. All causes of diabetes ultimately lead to hyperglycemia, which is the hallmark of this disease syndrome. Several clinical subclasses are recognized, including: Type I (insulin-dependent or IDDM), Type II (non-insulin-dependent diabetes mellitus), maturity-onset diabetes of the young (MODY) and gestational diabetes.

An emerging model for obesity-induced Type II diabetes is based on forms of lipodystrophic diabetes and hypothesizes that diabetes can result from insufficient expansion of adipose in response to energy excess. In studies carried out by Kim et al. (Kim et al. (2000) *J. Biol. Chem.* 275:8456–60), fatless mice were created using a P2 enhancer/promoter that targeted adipocyte-specific transgene expression of a dominant-negative protein termed A-ZIP/F1. This protein contains a domain that has been shown to inhibit the DNA binding and function of certain bZIP transcription factors. Despite the virtual absence of adipose tissue, the transgenic mice develop diabetes. It is presumed that if the adipose organ is unable to respond adequately to excess calories, then the excess is stored in the liver and muscle.

Overall, in the United States the prevalence of diabetes is about 2 to 4 percent, with IDDM comprising 7 to 10 percent of all cases. The prevalence of IDDM is probably more accurate than the estimates for Type II diabetes. This is due at least in part to the relative ease of ascertainment of IDDM, while many patients with Type II diabetes are asymptomatic and thus this form of the disease goes undiagnosed. Type II diabetes, the most common form of diabetes found in the United States, is characterized by a later age of onset, insulin resistance and impaired insulin secretion. Obesity and increased hepatic glucose output are also associated with Type II diabetes. Indeed, in the United States, 80 to 90 percent of Type II diabetes patients are obese. The precise role of obesity in the causes of Type II diabetes and the development of complications associated with diabetes remains equivocal.

Type II diabetes has been shown to have a strong familial transmission: 40% of monozygotic twin pairs with Type II diabetes also have one or several first degree relatives affected with the disease. Barnett et al. (1981) *Diabetologia* 20:87–93. In the Pima Indians, the relative risk of becoming diabetic is increased twofold for a child born to one parent who is diabetic, and sixfold when both parents are affected (Knowler, W. C., et al. (1988) *Genetic Susceptibility to Environmental Factors. A Challenge for Public Intervention,* Almquist & Wiksele International: Stockholm. p. 67–74). Concordance of monozygotic twins for Type II diabetes has been observed to be over 90%, compared with approximately 50% for monozygotic twins affected with Type I diabetes (Barnett, A. H., et al. (1981) *Diabetologia* 20(2):87–93). Non-diabetic twins of Type II diabetes patients were shown to have decreased insulin secretion and a decreased glucose tolerance after an oral glucose tolerance test (Barnett, A. H., et al. (1981) *Brit. Med. J.* 282:1656–1658).

Central fat, particularly intra-abdominal adipose tissue (IAAT), is associated with increased risk for Type II diabetes (Vague, J. (1996) *Obesity Res.* 4(2):201–3; Kissebah, A. H., et al. (1982) *J. of Clinical Endocrinology & Metabolism* 54(2):254–60; Bjomtorp, P. (1992) *Obesity* 579–586).

Diabetes is a complex syndrome affected not only by familial transmission but by environmental factors as well (Kahn, C. R. et al. (1996) *Ann. Rev. of Med.* 47:509–31; Aitman, T. J. and Todd, A. J. (1995) *Baillieres Clin. Endocrinology & Metabolism* 9(3):631–56). There is a high prevalence of the disease in world populations. Expression is strongly age-dependent and the etiology is heterogeneous. The combined effect of these factors makes mapping the genes responsible for Type II diabetes particularly challenging. For example, a major pitfall for using linkage analysis with a complex trait such as diabetes is the difficulty in establishing transmission models. The high prevalence of the disease in world populations, reduced penetrance, and the presence of phenocopies each contributes to reducing the power of linkage studies. Sib pair studies and the transmission disequilibrium test, non-parametric methods which do not require a model for mode of inheritance, are hampered by heterogeneity and the large number of phenocopies expected for such a complex common disease. A number of published findings suggest linkage of diabetes to chromosome 20q (Ji et al. (1997) *Diabetes* 46:876–81; Bowden, D. W., et al. (1997) *Diabetes* 46:882–86; Velho et al. (1997) *Diabetes and Metabolism* 23:34–37; and Zouali et al. (1997) *Human Molec. Genet.* 6:1401–1408), but definition of a locus linked to susceptibility to Type II diabetes has thus far been unsuccessful.

Segregation analyses of Type II diabetes or related phenotypes have provided support for a major gene (Hanson, R. L., et al. (1995) *Amer. J. of Human Genetics* 57:(1):160–70; Serjeantson, S. W. and Zimmet, P. (1991) *Baillieres Clin. Endocrinology & Metabolism* 5(3):477–93; Elston, R. C., et al. (1974) *Amer. J. of Human Genetics* 26(1):13–34), though in some analysis models incorporating a major gene effect did not provide a significantly better fit than those with multifactorial inheritance, and more complex models were required to explain the data (Cook, J. T., et al. (1994) *Diabetologia* 37(12):1231–40; McCarthy, M. I. et al. (1994) *Diabetologia* 37(12):1221–30). Segregation analysis of Type II diabetes is complicated by the fact that disease expression is strongly age dependent and, in certain populations, by the increase in recent years of the incidence of the disease. Since obesity is commonly associated with Type II diabetes, it can also influence the familial relationships.

Mutations in hepatocyte nuclear factor-4α gene, which is located on chromosome 20, have been associated with maturity onset diabetes of the young (MODY), a form of Type II diabetes. Yamagata et al. (1996) *Nature*

384:458–460. However, genetic studies appear to have ruled out a role for the so-called MODY1 gene as a major late-onset Type II diabetes susceptibility gene. Velho and Froguel (1998) *Eur. J. Endocrinol.* 138:233–239. Ji et al. ((1997) *Diabetes* 46:876–881) tested whether a gene or genes in the MODY1 region of chromosome 20 contributes to the development of Type II diabetes. They reported a possible linkage between Type II diabetes and markers D20S119, D20S178, and D20S197. Bowden et al. ((1997) *Diabetes* 46:882–886) also examined the potential contribution of MODY genes to Type II diabetes susceptibility in African American and Caucasian Type II diabetes-affected sibling pairs with a history of adult-onset diabetic nephropathy. While a linkage was seen among Caucasian sib pairs between MODY1-linked marker D20S197 and Type II diabetes, no evidence for linkage of MODY1 marker to Type II diabetes in Africa-American sib pairs was observed.

Linkage disequilibrium (LD) analysis is a powerful tool for mapping disease genes and may be particularly useful for investigating complex traits. LD mapping is based on the following expectations: for any two members of a population, it is expected that recombination events occurring over several generations will have shuffled their genomes, so that they share little in common with their ancestors. However, if these individuals are affected with a disease inherited from a common ancestor, the gene responsible for the disease and the markers that immediately surround it will likely be inherited without change, i.e., will be identical by descent (IBD), from that ancestor. The size of the regions that remain shared, or IBD, are inversely proportional to the number of generations separating the affected individuals and their common ancestor. Thus, established populations are suitable for fine scale mapping and recently founded ones are appropriate for using LD to roughly localize disease genes. Because isolated populations typically have had a small number of founders, they are particularly suitable for LD approaches.

LD analysis has been used in several positional cloning efforts. Kerem et al. (1989) *Science* 245:1073–1080; Hastbacka et al. (1992) *Nat. Genet.* 2:204–211; and Hastbacka et al. (1994) *Cell* 78:1073–1087. However, the initial localization had been achieved using conventional linkage methods. Positional cloning is the isolation of a gene solely on the basis of its chromosomal location, without regard to its biochemical function. It has been proposed that LD mapping could be used to screen the human genome for disease loci, without conventional linkage analysis. Lander and Botstein (1986) *Proc. Natl. Acad. Sci. USA* 83:7353–7357. This approach was not practical until a set of mapped markers covering the genome became available. Weissenbach et al. (1992) *Nature* 359:794–801. These markers include microsatellites. Microsatellites are highly polymorphic markers based on variable numbers of short tandem repeats of 1 to 6 base pairs, whose abundance has been estimated at an average of one in every 6 kilobase of human genomic sequence. Thousands of microsatellites have been characterized. Since unique nucleotide sequences flanking microsatellites have been identified, and since each locus is small enough to be analyzed using polymerase chain reaction, microsatellite analysis has emerged as a powerful tool for genetic analysis.

Even with the availability of mapped markers, mapping of complex traits has proven difficult. It has been suggested that mapping of complex traits, such as susceptibility to Type II diabetes, would require very large sample sizes and extremely dense marker maps, making whole genome population-based studies with relatively small sample sizes have been characterized unfeasible. Risch and Merikangas (1996) *Science* 273:1516–1517. Instead, it was suggested that very large sample sizes and extremely dense marker maps could be needed for whole genome association studies of complex traits, using standard association tests. However, an absence of LD around disease genes was assumed; this assumption is valid in large, heterogeneous study populations but not in genetically homogeneous ones. In homogeneous populations, LD may be maintained for distances of several centimorgans (cM) around disease genes due to the fact that affected individuals are IBD for the regions around disease genes. Additionally, in such populations one may test for association using methods that differentiate such IBD regions from background levels of haplotype sharing (Jorde, L. B. (1995) *Amer. J. of Human Genetics* 56(1):11–14).

Identification of Type II diabetes gene(s) is of major interest, with enormous diagnostic and therapeutic potential. The foregoing discussion highlights the difficulties which have been encountered in attempts to identify genetic loci which contribute to Type II diabetes. Indeed, genome-wide scans by several groups have revealed that Type II diabetes is far more complex and heterogeneous than many had originally thought. Because a genetic locus has not yet been identified which is unequivocally associated with Type II diabetes, methods for detecting susceptibility to this disease are lacking. In addition, methods for diagnosing the disease are currently insufficient.

The present invention addresses the need for diagnostic tools and methods for identifying individuals who have or are at risk of developing Type II diabetes.

Literature

Wang et al. (1999) *Genomics* 59:275–281; Hanson (1997) *Diabetes* 46:S1:51A; Mahtani et al. (1996) *Nature Genetics* 14:90–4; Hanis et al. (1996) *Nature Genetics* 13:161–6; Velho and Froguel (1998) *Eur. J. Endocrinol.* 138:233–239; Ji et al. ((1997) *Diabetes* 46:876–881); Venter et al. (2001) *Science* 1304.

SUMMARY OF THE INVENTION

The present invention provides isolated polynucleotides that include sequences from a region of human chromosome 20q between D20S119 and D20S195. The polynucleotides include polymorphisms associated with Type II diabetes and are useful as probes in screening for Type II diabetes. The invention further provides vectors and isolated host cells comprising the isolated polynucleotides. The invention further provides methods of detecting polymorphisms on chromosome 20q between D20S119 and D20S195, and methods of detecting a propensity to develop Type II diabetes, using the isolated polynucleotides of the invention.

BRIEF DESCRIPTION OF THE DRAWINGS

FIG. 2 is a chart showing genotyping data on seven distantly related members of the subject population which have Type II diabetes.

FIG. 5A provides the sequence of a 340-base pair fragment that encompasses SNP58, a single nucleotide polymorphism associated with Type II diabetes. FIG. 5B shows the sequence comprising the nucleotide sequence corresponding to SNP58 in a normal individual.

DETAILED DESCRIPTION OF THE INVENTION

Figure 1:
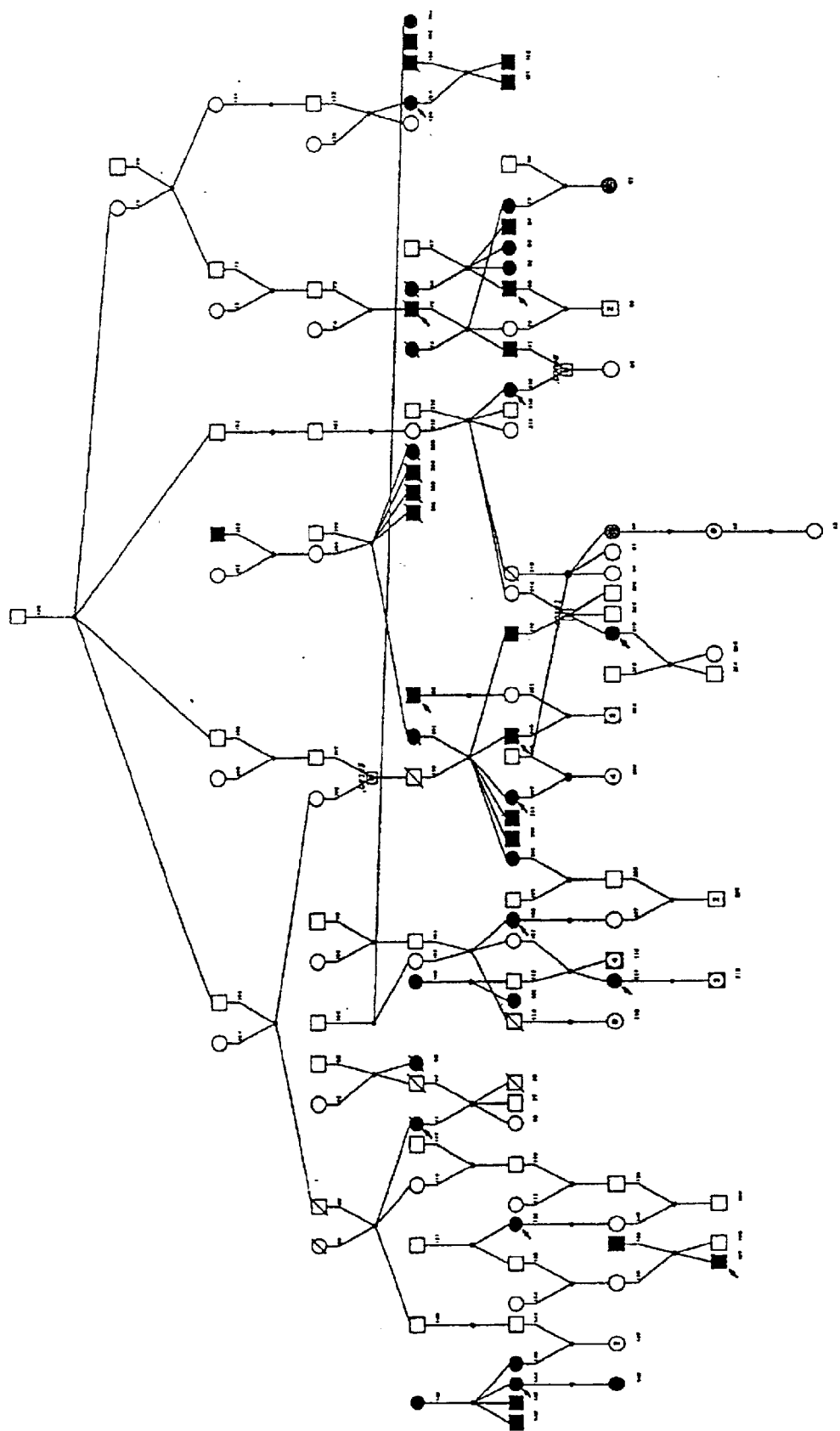
FIG. 1 is a pedigree chart showing families related to a single founder in the subject population. Individuals with diabetes are denoted by black symbols, deceased individuals by a diagonal slash. Squares indicate males; circles indicate females; diamond denote gender unknown. Arrows point to individuals whose genotype was determined. Boxed dots indicate consanguinity; numbers above boxed dots are kinship coefficients.

The present invention is based in part on the localization of a region associated with Type II diabetes to a small interval on chromosome 20q between D20S195 and D20S119. To achieve this localization, we have identified a population, a Bahamian island community, most of whose members are descended from a small number of founders. The diabetes in this population resembles Type II diabetes seen in the United States, i.e., it is characterized by adult age-of-onset and is associated with abdominal obesity. This population was analyzed by linkage disequilibrium using microsatellite markers. Attempts to identify a chromosomal region associated with Type II diabetes have heretofor been unsuccessful.

Localization of this Type II diabetes-associated interval in this population provides for a polynucleotide probe(s) comprising sequences included within the interval on chromosome 20q between D20S195 and D20S119 from a normal individual in the population who does not have Type II diabetes. This polynucleotide can thus serve as a hybridization probe in methods for detecting a polymorphism on chromosome 20q between D20S195 and D20S119 in the DNA of an individual. Accordingly, localization of this Type II diabetes-associated interval allows the development of methods for detecting a polymorphism on chromosome 20q between D20S195 and D20S119 in the DNA of an individual. Such methods make possible the identification of polymorphisms associated with Type II diabetes. Identification of this interval further allows identification and characterization of a gene(s) associated with Type II diabetes.

The invention provides isolated polynucleotides that include a polymorphism associated with Type II diabetes; vectors that include the polynucleotides; host cells that include the vectors; and primer sequences that are useful to amplify a polynucleotide comprising a polymorphism associated with Type II. Isolated polynucleotides that include a polymorphism associated with Type II diabetes are useful as diagnostic agents to identify individuals who are at risk of developing Type II diabetes.

The localization further allows development of methods for detecting a propensity in an individual to develop Type II diabetes, and methods for confirming a phenotypic diagnosis of Type II diabetes.

Definitions

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as "Current Protocols in Molecular Biology", eds. Ausubel et al., Greene Publishing and Wiley-Interscience: New York (1987) and periodic updates.

Techniques relating to linkage disequilibrium can be found in numerous publications, including, for example, Terwilliger (1995) Am. J. Hum. Genet. 56:777. The transmission disequilibrium test (TDT) technique has been described in, for example, Spielman et al. (1993) Am. J. Hum. Genet. 52:506.

Techniques relating to detection of mutations can be found in various publications, including for example, "Laboratory Methods for Detection of Mutations and Polymorphisms in DNA" (1997) CRC Press, G. R. Taylor, ed.; and "Laboratory Protocols for Mutation Detection" (1996) Oxford University Press, U. Landegrun, ed.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

"$T_m$" is the temperature in degrees Celsius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log[X^+] + 0.41 \, (\%G/C) - 0.61 \, (\%F) - 600/L$$

where [$X^+$] is the cation concentration (usually sodium ion, $Na^+$) in mol/L; (%G/C) is the number of G and C residues as a percentage of total residues in the duplex; (%F) is the percent formamide in solution (wt/vol); and L is the number of nucleotides in each strand of the duplex.

Stringent conditions for both DNA/DNA and DNA/RNA hybridization are as described by Sambrook et al. *Molecular Cloning, A Laboratory Manual,* 2nd Ed., Cold Spring Harbor Laboratory Press, Cold Spring Harbor, N.Y., 1989, herein incorporated by reference. For example, see page 7.52 of Sambrook et al. Stringent hybridization conditions are, for example, 50° C. or higher and 0.1×SSC (15 mM sodium chloride/01.5 mM sodium citrate) or lower. Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to in the instant methods.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18, Table 7.7.1. Preferably, default parameters for a given alignment program are used.

The term "a propensity to develop Type II diabetes", as used herein, intends a statistically significant increase in the probability of developing measurable symptoms of Type II diabetes in an individual having a particular genetic lesion(s) or polymorphism(s) compared with the probability in an individual lacking the genetic lesion or polymorphism.

"Polymorphism", as used herein, refers to a difference in the nucleotide sequence of a given region as compared to a nucleotide sequence in a homologous region of another individual, in particular, a difference in the nucleotide sequence of a given region which differs between individuals of the same species. Polymorphisms include single nucleotide differences, differences in sequence of more than one nucleotide, insertions, inversions and deletions. Thus, the term includes single nucleotide polymorphisms (SNPs); microsatellite allele size variations; insertions of one or more nucleotides; deletions of one or more nucleotides; inversions; and the like.

The term "polymorphism associated with Type II diabetes," as used herein, refers to a polymorphism that is found at a statistically significant higher frequency in individuals with Type II diabetes, and individuals with a propensity to develop Type II diabetes, compared to normal individuals (e.g., individuals without Type II diabetes).

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art.

A "substantially isolated" or "isolated" polynucleotide is one that is substantially free of the sequences with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides, which, by virtue of origin or manipulation: (1) are not associated with all or a portion of a polynucleotide with which it is associated in nature, (2) are linked to a polynucleotide other than that to which it is linked in nature, or (3) does not occur in nature.

The term "vector" refers to a DNA molecule that can carry inserted DNA and be perpetuated in a host cell. Vectors are also known as cloning vectors, cloning vehicles or vehicles. The term includes vectors that function primarily for insertion of a nucleic acid molecule into a cell, replication vectors that function primarily for the replication of nucleic acid, and expression vectors that function for transcription and/or translation of the DNA or RNA. Also included are vectors that provide more than one of the above functions.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in total DNA complement) to the original parent due to natural, accidental, or deliberate mutation. A host cell includes cells transfected with the polynucleotides of the present invention. An "isolated host cell" is one which is not associated with, i.e., has been physically dissociated with, the organism from which it was derived.

The terms "individual," "host," and "subject" are used interchangeably herein to refer to a vertebrate, preferably a mammal, more preferably a human. Mammals include, but are not limited to, murines, simians, humans, farm animals, sport animals, and pets.

As used herein, a "normal individual" includes a member of the subject Bahamian population who is a member of the pedigree family shown in FIG. 1, who does not have Type II diabetes and who does not carry a chromosome 20 allele for Type II diabetes. The "subject Bahamian population" is that described in Example 1, and includes members of the pedigree family shown in FIG. 1, as well as distantly related individuals whose DNA was examined in order to identify shared alleles. An isolated polynucleotide of the invention which is derived from a normal individual and which is contained within an isolated host cell is being deposited with Coriell Cell Repository. The term "normal individual" also includes any individual from any population who does not have a polymorphism associated with Type II diabetes in the region between D20S195 and D20S119, inclusive. As used herein, an "affected individual" is one who has symptoms of Type II diabetes. An isolated polynucleotide of the invention which is derived from an affected individual from the subject Bahamian population and which is contained within an isolated host cell is being deposited with Coriell Cell Repository.

An isolated polynucleotide comprising sequences from a region on chromosome 20q between D20S119 and D20S195 which serves as a "normal" control is derived from 1) a "normal" individual, as described above; and/or 2) the normal homolog of the region on chromosome 20q between D20S119 and D20S195 from a heterozygous, affected individual from the subject Bahamian population.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

The terms "transformation," "transfection," and "genetic transformation" are used interchangeably herein to refer to the insertion or introduction of an exogenous polynucleotide into a host cell, irrespective of the method used for the insertion, for example, lipofection, transduction, infection, electroporation, CaPO$_4$ precipitation, DEAE-dextran, particle bombardment, etc. The exogenous polynucleotide may be maintained as a non-integrated vector, for example, a plasmid, or alternatively, may be integrated into the host cell genome. The genetic transformation may be transient or stable.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a polymorphism" includes a plurality of such polymorphisms and reference to "the polynucleotide" includes reference to one or more polynucleotides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Isolated Polynucleotides Comprising a Region on Chromosome 20Q Between D20S195 and D20S119

The present invention provides isolated polynucleotides comprising a region of chromosome 20q between D20S195 and D20S119; and isolated polynucleotides comprising a polymorphism associated with Type II diabetes, which polymorphism is located in a region between D20S195 and D20S119; and isolated primer sequences that are useful to amplify a polynucleotide comprising a polymorphism associated with Type II. These polynucleotides comprise at least one polymorphism associated with Type II diabetes, and/or can be used to detect at least one polymorphism associated with Type II diabetes, and therefore have utility in a variety of diagnostic methods, as described herein.

Accordingly, the present invention encompasses isolated polynucleotides comprising a region of chromosome 20q between D20S195 and D20S119, isolated polynucleotides comprising a polymorphism associated with Type II diabetes, which polymorphism is located in a region between D20S195 and D20S119, vectors containing these polynucleotides, host cells containing these polynucleotides, and compositions comprising these polynucleotides. These polynucleotides are isolated and/or produced by chemical and/or recombinant methods, or a combination of these methods. Unless specifically stated otherwise, "polynucleotides" shall include all embodiments of the polynucleotide of this invention. These polynucleotides are useful as probes, primers, in expression systems, and in diagnostic methods as described herein.

An isolated polynucleotide of the present invention comprises a sequence contained within a region flanked by microsatellite markers D20S195 and D20119, (SEQ ID NO:1 and SEQ ID NO:2, respectively). In one embodiment, the invention provides isolated polynucleotides comprising a region of chromosome 20q between D20S195 and D20S119 from a normal individual. In other embodiments, the invention provides isolated polynucleotides comprising a region of chromosome 20q between D20S195 and D20S119 that include a polymorphism associated with Type II diabetes.

The isolated polynucleotide need not include the entire region of chromosome 20q between D20S195 and D20S119 as long as at least one polymorphism associated with Type II diabetes is included within the polynucleotide fragment, or as long as the polynucleotide fragment can detect at least one polymorphism associated with Type II diabetes. Using the oligonucleotide primers derived from SEQ ID NO:1 and SEQ ID NO:2, polynucleotides of about 300 kb (kilo base pairs) to about 1000 kb can be identified and isolated. Oligonucleotide primers derived from SEQ ID NO:1 and SEQ ID NO:2 which are useful in amplifying microsatellite markers D20S195 and D20S119, respectively, are those which flank the repeat sequence. For example, oligonucleotide primers which would amplify D20S119 include the following: 5' agctaactgacacagtttcag 3' (nucleotides 1–21 of SEQ ID NO:2); and 5' agtacattttctggcacttga 3' (complement of nucleotides 300 to 320 of SEQ ID NO:2).

Accordingly, a polynucleotide of the invention may be about 20, about 25, about 30, about 35, about 40, about 45, about 50, about 60, about 70, about 80, about 90, about 100, about 150, 200, 250, 300, 350, 400, 450, 500, 550, 600, 700, 800, 900, 1000, 1200, 1500, 1700, 2000, 3000, 4000, 5000, 6000, 7000 contiguous nucleotides or larger of the sequence flanked by microsatellite markers D20S195 and D20119, which can be amplified using oligonucleotide primers derived from SEQ ID NO:1 and SEQ ID NO:2.

Also encompassed in the present invention are isolated polynucleotides comprising 150 contiguous kilobases having at least about 50%, more preferably at least about 60%, more preferably at least about 70%, more preferably at least about 75%, more preferably at least about 80%, more preferably at least about 85%, even more preferably at least about 90%, even more preferably greater than 90% sequence identity to a sequence flanked by (i.e., comprised within) microsatellite markers DS20195 and DS20119, said polynucleotide comprising at least one polymorphism associated with Type II diabetes, and/or capable of detecting at least one polymorphism associated with Type II diabetes.

Also within the invention is an isolated polynucleotide at least about 15 nucleotides in length (preferably at least about 30, more preferably at least 100, more preferably at least about 150, even more preferably at least about 200, even more preferably at least about 250, even more preferably at least about 300, even more preferably at least about 400, and most preferably at least 450), including (a) a strand which hybridizes under stringent conditions to a DNA sequence flanked by (i.e., comprised within) microsatellite markers D20S195 and D20119 from an individual with Type II diabetes or a normal individual, (b) the complement thereof, or (c) a double-stranded DNA including both (a) and (b). Multiple copies of this isolated DNA (useful, for example, as a hybridization probe or PCR primer) can be produced by recombinant means, by transfecting a cell with a vector containing this DNA.

Microsatellite markers D20S107 and D20S170 are located between D20S195 and D20S119. As described in Example 2, Terwilliger analysis of D20S107 and D20S170 showed a maximum LOD score between these two markers. Accordingly, the invention encompasses isolated an isolated polynucleotide comprising the interval between D20S107 and D20S170 (SEQ ID NO:3 and SEQ ID NO:4, respectively). The invention further encompasses an isolated polynucleotide comprising sequences flanked by D20S195 and D20S107.

In addition to D20S107 and D20S170, over 100 markers which lie between D20S195 and D20S119 are known, and the sequences are available. The ABI Prism Linkage Mapping Set is comprised of 400 markers that define a ~10 cM resolution human index map. The loci have been selected from the Genethon linkage map based on chromosomal locations and heterozygosity. The map positions were generated from the CEPH genotype data used for the 1996 Genethon map. See, e.g., Davies et al. (1994) *Nature* 371:130–136; Weissenbach et 1. (1992) *Nature* 359:794–801; Gyapay et al. (1994) Genethon Human Genetic Linkage Map Nature Genet. 7: 246–339; and Dib et al. (1996) *Nature* 380:152–4.

The nucleotide sequences of D20S195, D20S119, D20S107, D20S170, as well as these additional markers can be used to design oligonucleotide primers to prime PCR reactions to amplify polynucleotides between the markers, as described above. The amplified polynucleotides can be isolated by conventional means and, if desired, cloned into cloning and/or expression vectors. The amplified polynucleotides can be further tested for the presence of a sequences and/or polymorphisms associated with Type II diabetes. These isolated polynucleotides are encompassed by the present invention.

Specific polymorphisms associated with Type II diabetes and located in the region of chromosome 20q between D20S195 and D20S119 include a D20S107 microsatellite marker allele size of 214 base pairs. The present invention provides isolated polynucleotides that include the 214 bp allele of D20S107. The allele size of D20S107 is affected individuals (i.e., individuals with Type II diabetes) is 214 base pairs (bp). The allele sizes of D20S107 in normal individuals (i.e., individuals who do not have Type II diabetes) include 210 bp, 212 bp, 216 bp, and 218 bp.

An additional specific polymorphism associated with Type II diabetes and located in the region of chromosome 20q between D20S195 and D20S119 includes UABSNP58 (also referred to herein as "SNP58"). UABSNP58 (T/C) is located approximately 30 kb upstream of the KRML gene and is 5' of the rs1543379 SNP (A/G). The location of the rs1543379 SNP is found in Venter et al. (2001) *Science* 1304. The UABSNP58 is located in the sequence depicted in FIG. 5A, where the single nucleotide polymorphism, relative to unaffected, normal individuals, is denoted in bold type. The corresponding sequence in unaffected individuals is depicted in FIG. 5B.

Thus, in some embodiments, the invention provides an isolated polynucleotide comprising from about 10 to about 18, from about 18 to about 25, from about 25 to about 30, from about 30 to about 40, from about 40 to about 50, from about 50 to about 60, from about 60 to about 70, from about 70 to about 80, from about 80 to about 100, from about 100 to about 150, from about 150 to about 200, from about 200 to about 250, from about 250 to about 300, or from about 300 to about 325 contiguous nucleotides of the sequence set forth in SEQ ID NO:7. Of particular interest are polynucleotides that comprise the SNP58 sequence.

Isolated Primer Pairs

In some embodiments, the invention provides isolated nucleic acids that, when used as primers in a polymerase chain reaction, amplify an SNP58-containing polynucleotide. The amplified SNP58-containing polynucleotide is from about 20 to about 50, from about 50 to about 75, from about 75 to about 100, from about 100 to about 125, from about 125 to about 150, from about 150 to about 175, from about 175 to about 200, from about 200 to about 250, from about 250 to about 300, from about 300 to about 350 nucleotides in length, that comprises SNP58. The isolated nucleic acids that, when used as primers in a polymerase chain reaction, amplify an SNP58-containing polynucleotide, are from about 10 to about 20, from about 20 to about 30, from about 30 to about 40, from about 40 to about 50, from about 50 to about 100, or from about 100 to about 200 nucleotides in length. Generally, the nucleic acids are used in pairs in a polymerase chain reaction, where they are referred to as "forward" and "reverse" primers.

Thus, in some embodiments, the invention provides a pair of isolated nucleic acid molecules, each from about 10 to 200 nucleotides in length, the first nucleic acid molecule of the pair comprising a sequence of at least 10 contiguous nucleotides having 100% sequence identity to the nucleic acid sequence set forth in SEQ ID NO:7 and the second nucleic acid molecule of the pair comprising a sequence of at least 10 contiguous nucleotides having 100% sequence identity to the reverse complement of the nucleic acid sequence set forth in SEQ ID NO:7, wherein the sequence of the second nucleic acid molecule is located 3' of the nucleic acid sequence of the first nucleic acid molecule in SEQ ID NO:7. The primer nucleic acids are prepared using any known method, e.g., automated synthesis, and the like.

In some embodiments, the first and/or the second nucleic acid molecules comprises a detectable label. Suitable labels include fluorochromes, e.g. fluorescein isothiocyanate (FITC), rhodamine, Texas Red, phycoerythrin, allophycocyanin, 6-carboxyfluorescein (6-FAM), 2', 7'-dimethoxy-4', 5'-dichloro-6-carboxyfluorescein (JOE), 6-carboxy-X-rhodamine (ROX), 6-carboxy-2', 4', 7', 4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In general, the first and second nucleic acid molecules are located 5' and 3', respectively, of the region of SEQ ID NO:7 corresponding to the location of SNP58. The pair of nucleic acid molecules primes amplification of a portion of a human nucleic acid molecule comprising a nucleotide position corresponding to a mutation associated with Type II diabetes when used in a polymerase chain reaction with a human nucleic acid molecule as a template. One non-limiting example of such a pair of nucleic acids is found in Example 3, and the sequences are provided as SEQ ID NO:5 and :6. Those skilled in the art, given the sequence provided in FIG. 5A, can readily prepare additional nucleic acids that amplify a polynucleotide encompassing SNP58.

Kits

The invention further provides a kit comprising a pair of nucleic acids as described above. The nucleic acids are present in a suitable storage medium, e.g., buffered solution, typically in a suitable container. The kit includes the pair of nucleic acids, and may further include a buffer; reagents for polymerase chain reaction (e.g., deoxynucleotide triphosphates (dATP, dTTP, dCTP, and dGTP), a thermostable DNA polymerase, a buffer suitable for polymerase chain reaction, a solution containing $Mg^{2+}$ ions (e.g., $MgCl_2$), and other components well known to those skilled in the art for carrying out a polymerase chain reaction). The kit may further include instructions for use of the kit, which instructions may be provided in a variety of forms, e.g., as printed information, on a compact disc, and the like. The kit may further include reagents necessary for extraction of DNA from a biological sample (e.g., biopsy sample, blood, and the like) from an individual. The kits are useful in diagnostic applications, as described in more detail below. For example, the kit is useful to determine whether a given DNA sample isolated from an individual, comprises a polymorphism associated with Type II diabetes.

Identification of a Region on Chromosome 20q Associated with Type II Diabetes

To identify a polymorphism in a region of chromosome 20q between D20S195 and D20S119 as being associated with Type II diabetes, an iterative approach combining genome screening and localization techniques based on the findings from the genome screening can be followed. The following steps can be performed.

Step 1. Complete genotyping can be carried out, using a full set of genome screening markers on the subjects and their relatives, using markers shown in FIGS. 3A and 3B.

Step 2. The genome screening results can be analyzed using various methods for detecting association between diabetes and marker loci, including but not limited to, transmission disequilibrium tests (TDT, Spielman et al. (1992) *Nature Genetics* 1:82–3), the linkage disequilibrium analysis of Terwilliger (Terwilliger (1995) *Amer. J. of Human Genetics* 56(3):777–787), and the ancestral haplotype reconstruction method (Service et al. (1997) *J. of Human Genetics* 159:A236).

Based on computer simulations, we have a high probability of detecting diabetes loci with the Bahamian study population, even if diabetes is highly etiologically heterogeneous in the population. Subjects are generally analyzed in blocks of 20. Steps 1 and 2 are performed each time that a block of 20 new subjects is assembled. However, steps 1 and 2 can be performed with progressively larger samples until the data from the entire genome screening set have been analyzed. The analyses of the genome screening data are used to identify genome regions that should be investigated more intensively, rather than to test for statistically significant associations. For this reason, we used an inclusive threshold for identifying these regions, namely a p-value (in any of the three tests) of 0.05.

Step 3. Additional genotyping experiments can be performed in the regions identified in Step 2. For regions identified via the TDT or linkage disequilibrium of Terwilliger additional markers are typed that flank the original markers of interest at distances of about 1 cM.

For regions identified via the above-mentioned tests, one can type additional markers lying between the markers that form the initially detected haplotype, and the others flanking the original markers at distances of about 1 cM. This plan is feasible given the current density of polymorphic markers and the placement of such markers on the genetic and physical maps.

We analyzed the genotyping data in these highlighted regions to test for statistically significant associations. For determining the degree of significance we used conservative corrections for multiple testing. For association tests, guidelines for statistical significance have not been formally specified, as they have been for linkage tests; however, we followed an approach that is stringent.

The complete set of genotyping data (using the genome screening set of markers) can be re-analyzed each time the screen for a new block of subjects has been completed. In this case, it is possible that genome regions that initially met the thresholds for follow-up investigations will fail to meet these thresholds when more subjects are added. Such regions are then no longer targeted for intensive investigations. This strategy should minimize bias in the selection of regions to be targeted in the final round of analyses.

Figure 3A:
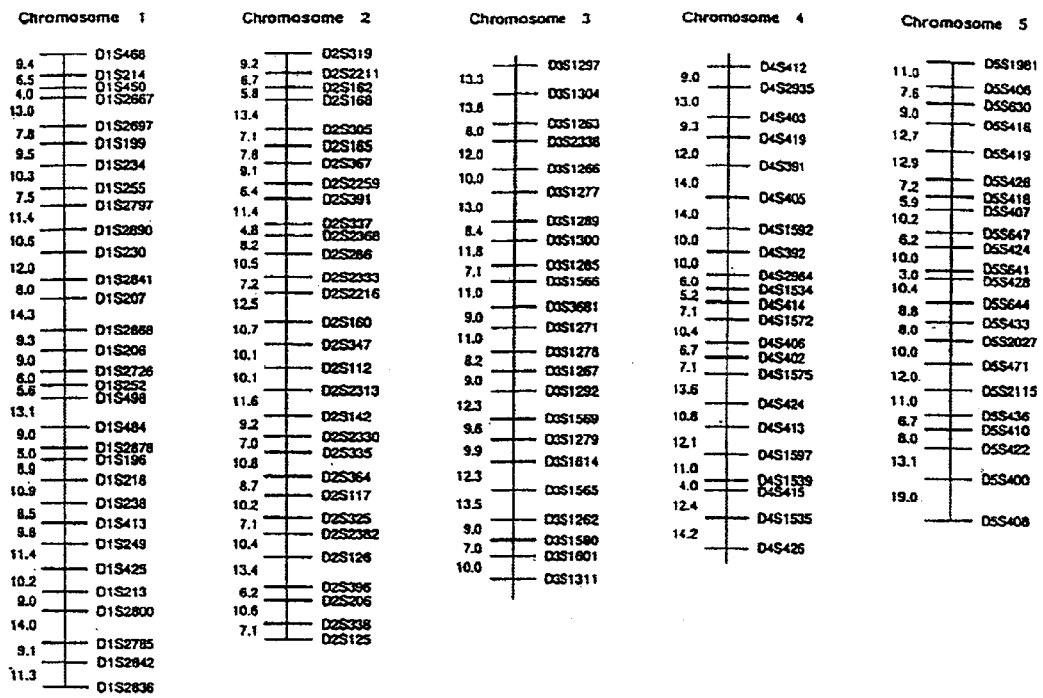
FIGS. 3A and 3B show chromosome map positions corresponding to the set of 400 primer pairs that define a 10 cM resolution linkage map.
Figure 3A:
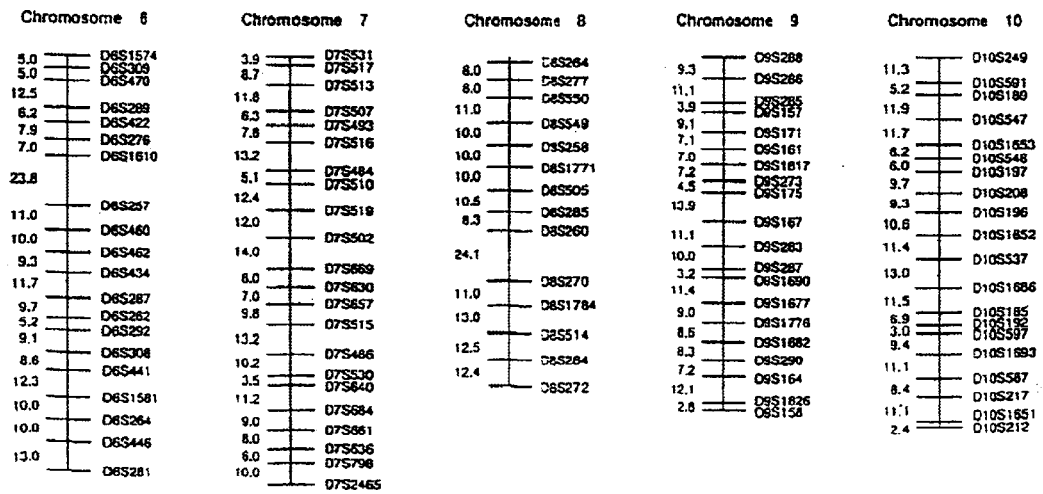
Figure 3B:
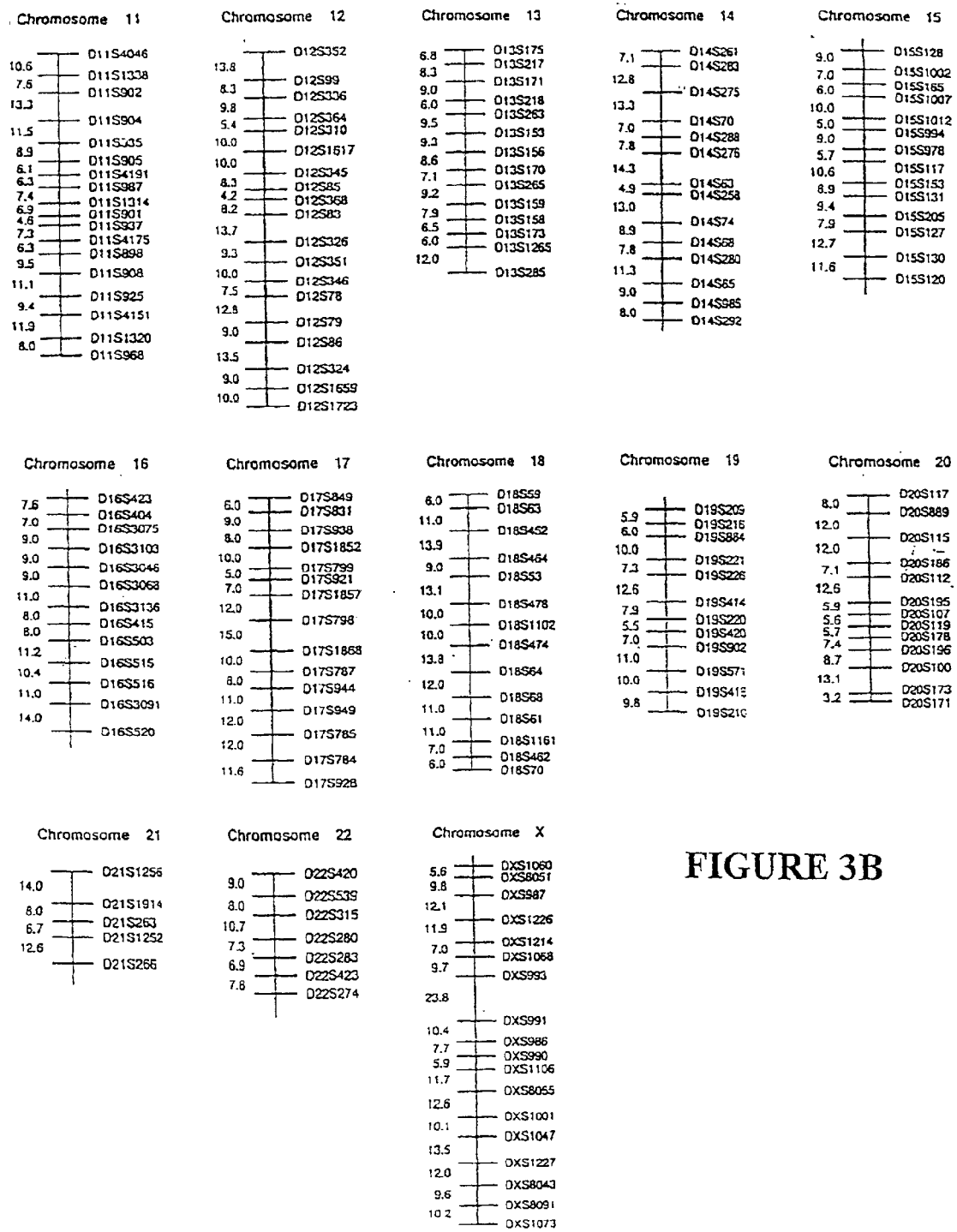

Genetic linkage analysis was performed using a set of highly polymorphic DNA markers, specifically microsatellite markers. The microsatellite markers which can be used for whole genome screening are described in the microsatellites Genethon map and are shown in FIGS. 3A and 3B. We initially chose to focus on chromosome 20, based on indications in the literature that one or more regions on chromosome 20 are potentially involved in MODY.

Microsatellite markers specific for chromosome 20 are shown in Table 2. Weissenbach et al. (1992) *Nature* 359:794–801; and Weber et al. (1993) *Am. J. Hum. Gen.* 53:1079–1095. Oligonucleotide sequences which serve as primers for extending a polynucleotide sequence and which are specific for each microsatellite, are available in the Genome Data Bank. Using the set of markers shown in Table 2, we analyzed DNA samples from subjects with diabetes who are descendants of the founder population (pedigree shown in FIG. 1). As described more fully in Example 2, we identified a segment less than 6 cM in length that localizes to a region on chromosome 20q between D20S195 and D20S119 and which is associated with Type II diabetes. Using different sets of microsatellite markers, other regions of the genome can be analyzed for a linkage to susceptibility to Type II diabetes. In addition, using microsatellite markers within the interval flanked by D20S119 and D20S195, one can further narrow the interval, using the methods described herein. Any of a variety of polymorphisms, including, but not limited to, microsatellite alleles, single-nucleotide polymorphims, inversions, deletions of one or more nucleotides, insertions of one or more nucleotides, changes in the nucleotide sequence that alter an encoded amino acid sequence, changes in the nucleotide sequence that affect expression (e.g., transcription) of a coding region, changes in the nucleotide sequence that affect translation of a coding region, and the like.

Preparation of Polynucleotides of the Invention

The polynucleotides of this invention can be obtained using any known method, including, but not limited to, chemical synthesis, recombinant methods, and a PCR.

PCR allows reproduction of DNA sequences. PCR technology is well known in the art and is described in U.S. Pat. Nos. 4,683,195, 4,800,159, 4,754,065 and 4,683,202, as well as PCR: *The Polymerase Chain Reaction,* Mullis et al. eds., Birkauswer Press, Boston (1994). Other methods for amplifying a template polynucleotide are known to those skilled in the art and can be used to prepare the polynucleotides of the present invention.

As described in Example 2, the isolated polynucleotides of the present invention can be identified using oligonucleotide primer pairs derived from the sequences given in SEQ ID NO:1 and SEQ ID NO:2 to identify a region of chromosome 20q between D20S195 and D20S119. Alternatively, an isolated polynucleotide can be identified using oligonucleotide primer pairs derived from the sequences given in SEQ ID NO:3 and SEQ ID NO:4, corresponding to D20S107 and D20S170, respectively. In addition, oligonucleotide primers derived from sequences of additional microsatellite markers within the region flanked by D20S195 and D20S119 can be used to identify an isolated polynucleotide of the present invention. Amplification can be achieved by any known method, including, but not limited to, a polymerase chain reaction. Polynucleotides which serve as templates for amplification can be obtained from an individual having Type II diabetes, or a normal individual.

One of skill in the art will recognize that a variety of oligonucleotide primer pairs can be used to identify polynucleotides comprising a region of chromosome 20q between D20S195 and D20S119. For example, by selecting oligonucleotide primers which hybridize to sequences proximal to but 5' or 3' of oligonucleotide primer sequences derived from SEQ ID NO:1 and SEQ ID NO:2, one can amplify a polynucleotide comprising a region of chromosome 20q between D20S195 and D20S119. Alternative primer pairs can be overlapping or non-overlapping with oligonucleotide sequences derived from SEQ ID NO:1 and SEQ ID NO:2.

Oligonucleotide primers derived from SEQ ID NO:1 and SEQ ID NO:2 can also be used as primers to determine a nucleotide sequence of a region of chromosome 20q between D20S195 and D20S119, using well known techniques of determining a nucleotide sequence, including, but not limited to, the dideoxy chain termination method. For example, an oligonucleotide having the sequence 5' gcacacatacaccoctgaaaa 3' (nucleotides 331 to 351 of SEQ ID NO:1) can be used to prime synthesis for sequencing from D20S195 in the direction of D20S119; and an oligonucleotide having the sequence 5' tgaaactgtgtcagttagct 3' (complementary to nucleotides 1–20 of SEQ ID NO:2) can be used to prime synthesis for sequencing from D20S119 in the direction of D20S195. Similarly, oligonucleotide primers having sequences derived from SEQ ID NO:3 and SEQ ID NO:4 can be used to prime synthesis for sequencing between D20S107 and D20S170, between D20S195 and D20S107, and between D20S119 and D20S170. Using the sequence data thus obtained using this technique, also called "primer walking", further oligonucleotide primers can be designed and additional nucleotide sequence information obtained. The sequence date thus obtained can be used to design additional primers for amplifying sequences comprised within D20S195 and D20S119. Using this method, smaller isolated polynucleotides comprised within D20S195 and D20S119 can be obtained.

In addition to D20S107 and D20S170, several microsatellite markers which lie between D20S195 and D20S119 are known and the sequences are available. The nucleotide sequences of D20S195, D20S119, D20S107, D20S170, as well as these additional markers can be used to design oligonucleotide primers to prime PCR reactions to amplify polynucleotides between the microsatellite markers, as described above. In this way, a "PCR contig library", i.e., a library of adjacent PCR amplification products, can be generated, covering the entire region between D20S195 and D20S119. The amplified polynucleotides can be isolated by conventional means and, if desired, inserted into cloning and/or expression vectors. The amplified polynucleotides can be further tested for the presence of sequences and/or polymorphisms associated with Type II diabetes. Ascertainment of whether an isolated polynucleotide is associated with Type II diabetes can be performed using the methods described in Example 2.

As described in Example 3, a polynucleotide that includes a polymorphism associated with Type II diabetes can be generated using pairs of nucleic acids that, when used in a polymerase chain reaction, amplify a polynucleotide that includes a polymorphism associated with Type II diabetes. DNA is obtained from an individual (or mRNA is obtained; and the mRNA is reverse transcribed into DNA), and the DNA is amplified using a primer pair that flanks a polymorphism associated with Type II diabetes. As one non-limiting example, primers such as those having sequences set forth in SEQ ID NO:5 and :6 can be used.

The polynucleotides can also be generated using methods known in the art, such as chemical synthesis, site-directed mutagenesis, and/or recombinant methods.

Methods of chemical polynucleotide synthesis are well known in the art and need not be described in detail herein. One of skill in the art can use the sequences provided herein and a commercial DNA synthesizer to produce a desired DNA sequence.

For preparing the polynucleotides of the invention using recombinant methods, a polynucleotide comprising a sequence comprised within D20S195 and D20S119 can be inserted into a suitable vector, and the vector in turn can be introduced into a suitable host cell for replication and amplification. Identification of the isolated polynucleotide as being comprised within D20S195 and D20S119 can be achieved as described above, using PCR primer pairs of known sequence, such as those derived from SEQ ID NO:1 and SEQ ID NO:2, as described herein, or using primer pairs identified by "primer walking", as described above. Polynucleotides may be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Cloning and Expression Vectors Comprising an Isolated Polynucleotide of the Invention The present invention further includes a variety of vectors (i.e., cloning and expression vectors) having cloned therein a polynucleotide(s) comprising a region of chromosome 20q between D20S195 and D20S119, as described above; and vectors comprising a polymorphism associated with Type II diabetes, as described above. These vectors can be used for expression of recombinant polypeptides as well as a source of polynucleotides comprising a region of chromosome 20q between D20S195 and D20S119 and/or a polymorphism associated with Type II diabetes. Cloning vectors can be used to obtain replicate copies of the polynucleotides of the invention that they contain, or as a means of storing the polynucleotides in a depository for future recovery. Expression vectors (and host cells containing these expression vectors) can be used to obtain polypeptides produced from the polynucleotides they contain. They may also be used where it is desirable to express polypeptides, encoded by an operably linked polynucleotide, in an individual, such as for eliciting an immune response via the polypeptide(s) encoded in the expression vector(s). Suitable cloning and expression vectors include any known in the art, e.g., those for use in bacterial, mammalian, yeast and insect expression systems. Specific vectors and suitable host cells are known in the art and need not be described in detail herein. For example, see Gacesa and Ramji, *Vectors*, John Wiley & Sons (1994).

Various methods for cloning DNA fragments are known in the art and can be used. These methods include, for example, cloning into mammalian artificial chromosomes (MAC), human artificial chromosomes (HAC), yeast artificial chromosomes (YAC), bacterial artificial chromosomes (BAC), bacteriophage vectors such as P1, bacterial vectors, viral vectors (e.g., adenoviral vectors, vaccinia vectors, adenoassociated viral vectors), plasmids, cosmids, phagemids, and the like. "Current Protocols in Molecular Biology", eds. Ausubel et al., Greene Publishing and Wiley-Interscience: New York (1987) and periodic updates; Ikeno et al. (1998) *Nature Biotech.* 16:431–439; Harrington et al. (1997) *Nat. Genet.* 15:345–355; and Burke et al. (1987) *Science* 236:806–812.

A vector comprising a polynucleotide of the invention can be introduced into a host cell and/or a target cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus). The choice of means of introducing vectors or polynucleotides of the invention will often depend on the host cell.

Isolated Host Cells Comprising a Region on Chromosome 20q Between D20S195 and D20S119

The invention further provides isolated host cells transfected or transformed with (i.e., comprising) the above-described isolated polynucleotides, or above-described expression or cloning vectors of this invention. These cells are cultured in conventional nutrient media modified as appropriate for inducing promoters, selecting transformants, or amplifying the genes encoding the desired sequences.

The cells which are suitable for use in the methods of the present invention with respect to expression, transcriptional control, or for purposes of cloning and propagating a polynucleotide of the present invention can be prokaryotic or eukaryotic.

Host systems are known in the art and need not be described in detail herein. Prokaryotic hosts include bacterial cells, for example *E. coli, B. subtilis,* and mycobacteria. Among eukaryotic hosts are yeast, insect, avian, plant, *C. elegans* (or nematode) and mammalian cells. Examples of mammalian cells are COS cells, mouse L cells, Chinese hamster ovary (CHO) cells, human embryonic kidney (HEK) cells, human adipocyte cell lines, and African green monkey cells. *Xenopus laevis* oocytes, or other cells of amphibian origin, may also be used. Hybrid cells can also be used and include, but are not limited to, human cell-hamster somatic cell hybrids. Also suitable as host cells are mammalian cells lacking an endogenous region on chromosome 20q between D20S195 and D20S119.

Somatic cell hybrids formed from the fusion of human cells with those from a different species are readily available, for example from Coriell Cell Repositories, and methods for their production are known in the art.

Useful somatic cell hybrids between human cells and non-human cells are those which contain the portion of human chromosome 20 comprising sequences between D20S195 and D20S119, but lacking the homologous chromosomal region of the non-human species. Such hybrid cells can be analyzed for the presence of a region on chromosome 20q between D20S195 and D20S119. This can be achieved, for example, by amplifying DNA from the hybrid cell using oligonucleotide primers, as described above, or hybridization assays using a polynucleotide of the invention, as described above. Functional assays can also be used and include glucose uptake assays.

In these assays, uptake of glucose is measured in the presence of insulin to stimulate glucose uptake. If a hybrid cell contains a region on chromosome 20q between D20S195 and D20S119, derived from a normal individual, that is involved with glucose metabolism, then glucose uptake in the presence of added insulin will be significantly above background for the cell. If a hybrid cell contains a region on chromosome 20q between D20S195 and D20S119, derived from an individual with Type II diabetes, and the region is involved with glucose metabolism, then glucose uptake will be at background levels for the cell, or will be at a significantly lower level than for the normal cell.

An example of a glucose uptake assay is as follows. Adipocytes ($1-2 \times 10^5$ cells/ml) are suspended in Krebs-Ringer phosphate buffer with 3% (0.45 M) bovine serum albumin and 1.5 mM pyruvate and incubated in plastic tubes with or without insulin (1 nM final concentration) at 37° C. for 15 minutes. Cells are incubated with 6.0 iCi of 1-[$^3$H]-2-deoxy-D-glucose (final concentration is 34 $\mu$M) added to the cell mixture and incubated for 3 minutes at 37° C. At the end of the 3 minute incubation, the cells are separated from the liquid by centrifugation through dinonyl pthalate oil. The oil layer is then removed and the 1-[$^3$H]-2-deoxy-D-glucose associated with the oil layer is quantitated by liquid scintillation counting. Nonspecific glucose transport is determined in the presence of 50 $\mu$M cytochalasin B.

Diagnostic Methods

The above-described isolated polynucleotides can be used for a wide variety of purposes, which will vary with the desired or intended result. Accordingly, the present invention includes methods using the isolated polynucleotides of the invention, which have been described above.

Methods of Detecting a Polymorphism on Chromosome 20q Between D20S195 and DS20S119

The present invention provides methods for detecting a polymorphism on chromosome 20q between D20S195 and D20S119. Any of a number of known methods can be used to detect a polymorphism in this region. As one example, a polynucleotide sample derived from an individual is analyzed for specific hybridization to a probe, under stringent hybridization conditions, wherein said probe comprises a polynucleotide comprising a sequence which is contained within in a region flanked by microsatellite markers D20S195 and D20S119. If the probe is derived using template polynucleotide from an individual with Type II diabetes, then specific hybridization is indicative of a polymorphism in this region. If the probe is derived from a normal individual, then lack of hybridization is indicative of a polymorphism in this region.

A polynucleotide sample can be derived from an individual using established methods. Depending on the method used for analyzing the polynucleotide sample, it may be desirable to extract the polynucleotide from the biological sample. This can be accomplished by any known means, for example, digesting a cell sample with proteinase K then extracting the polynucleotide.

Any of a number of techniques known to those skilled in the art can be used to detect a polymorphism in a region on chromosome 20q between D20S195 and D20S119, using an isolated polynucleotide of the invention. These include, but are not limited to, direct sequencing of the interval from affected individuals (Chadwick et al. (1996) *Biotechniques* 20:676–683); and hybridization with one or more probes derived from a region on chromosome 20q between D20S195 and D20S119, including allele-specific oligonucleotide hybridization (Wong and Senadheera (1997) *Clin. Chem.* 43:1857–1861). The region being detected can optionally be amplified by known techniques, including, but not limited to, a polymerase chain reaction. Other analytical techniques include, but are not limited to, single-strand conformation analysis; restriction length polymorphism (RFLP) analysis; enzymatic mismatch cleavage techniques such as glycosylase mediated polymorphism detection (Vaughan and McCarthy (1998) *Nucl. Acids Res.* 26:810–815); heteroduplex PCR (Deuter and Muller (1998) *Hum. Mutat.* 11:84–89); and fiberoptic DNA sensor array techniques (Healey et al. (1997) *Anal. Biochem.* 251:270–279). Automated methods of detecting polymorphisms have been developed and can be used in the methods of the present invention. See, for example, Marshall and Hodgson (1998) *Nature Biotechnol.* 16:27–31. Other methods include, for example, PCR-RFLP. Hani et al. (1998) *J. Clin. Invest.* 101:521–526.

In one embodiment, the method comprises hybridization of selected oligonucleotide primers, such as those derived from SEQ ID NO:1 and SEQ ID NO:2, to a DNA sample derived from the individual to be tested, followed by amplification by any known technique, for example, a polymerase chain reaction (PCR). The polymorphic amplified fragments are then separated according to their size by electrophoresis on acrylamide denaturing gels, transferred onto a membrane, such as a nylon membrane, and, after treating the membrane to reduce non-specific binding, hybridized with microsatellite probes comprising a detectable label. Alternatively, after separating the samples on gels, the sizes of the amplification products are compared visually for differences indicative of the presence of one or more polymorphisms associated with Type II diabetes. Alternatively, automated genotyping (utilizing fluorescent dyes and including size standards in each run) can be used to detect size differences between amplified sequences.

In some embodiments, the methods involve detecting the presence of SNP58 in an individual. Whether an individual harbors SNP58 in the individual's DNA can be determined using any known method, as described above. For example, a polynucleotide comprising SNP58 can be used as a hybridization probe under stringent hybridization conditions to determine whether the individual's DNA harbors SNP58. This technique is referred to in the art as allele-specific hybridization. For example, a polynucleotide of from about 10 to about 20, from about 20 to about 30, from about 30 to about 40, or from about 40 to about 50 nucleotides (or longer) that includes SNP58 is detectably labeled and is referred to as the SNP58 probe. The detectably labeled SNP58 probe is hybridized under stringent hybridization conditions with DNA from an individual being tested ("test DNA"). If the SNP58 probe hybridizes to the test DNA, then the test DNA includes SNP58.

The test DNA can also be amplified using primer pairs as disclosed herein, and the amplified polynucleotide subjected to sequencing to determine whether the SNP58 polymorphism is present.

Whether a given polymorphism is associated with Type II diabetes can be determined by analyzing a polynucleotide from a normal individual, a distantly related affected individual and an affected individual, all from the subject Bahamian population. A polymorphism found in a region on chromosome 20q between D20S195 and D20S119 in the normal individual would not be expected to be associated with Type II diabetes. However, a polymorphism in this region which is found in an affected individual from the pedigree family and in a distantly related affected individual, but which is not found in the normal individual would be expected to be associated with Type II diabetes. A polymorphism detected in this region in an individual who is not a member of the subject Bahamian population, would be expected to be associated with Type II diabetes if that polymorphism were absent from the homologous region in a normal individual.

Once it has been established that a given polymorphism is associated with Type II diabetes, an isolated polynucleotide comprising the polymorphism can be used to screen individuals for Type II diabetes.

Methods of Detecting a Propensity of an Individual to Develop Type II Diabetes

The present invention provides methods for detecting a propensity of an individual to develop Type II diabetes. The methods generally involve analyzing a polynucleotide sample derived from an individual for the presence of a DNA polymorphism on chromosome 20q between D20S195 and D20S119, wherein the polymorphism is associated with Type II diabetes. Methods of analysis are described above. Any known method can be used. Once a polymorphism associated with Type II diabetes has been detected in the DNA of an individual, the individual can then be monitored closely for the occurrence of symptoms associated with Type II diabetes. Symptoms may include polyuria and polydipsia. In addition to monitoring the individual, other measures may be taken, for example, modification of the individual's diet may be indicated.

Methods of Confirming a Phenotypic Diagnosis of Type II Diabetes

The present invention provides methods for confirming a phenotypic diagnosis of Type II diabetes. The methods generally involve analyzing a polynucleotide sample derived from an individual diagnosed as having Type II diabetes for the presence of a polymorphism on chromosome 20q between D20S195 and D20S119, wherein the polymorphism is associated with Type II diabetes. Methods of detecting a polymorphism on chromosome 20q between D20S195 and D20S119 have been described above.

Primer Walking in a Region on Chromosome 20q Between D20S195 and D20S119

Oligonucleotide primers having sequences derived from SEQ ID NO:1, SEQ ID NO:2, SEQ ID NO:3, and SEQ ID NO:4 can also be used as primers to determine a nucleotide sequence of a region of chromosome 20q between D20S195 and D20S119, using well known techniques of determining a nucleotide sequence, including, but not limited to, the dideoxy chain termination method. Using the sequence data thus obtained, further oligonucleotide primers can be designed and additional nucleotide sequence information obtained. Using this technique, also called "primer walking", information regarding polymorphisms in the region can be obtained, and coding sequences can be identified.

Identification of Coding Sequences in a Region on Chromosome 20q Between D20S195 and D20S119

The Type II diabetes-associated interval on chromosome 20q between D20S195 and D20S119 can be used to identify polynucleotide coding sequences which encode one or more polypeptides. The sequences of these polynucleotides can be determined, and conceptual translations made. The nucleotide sequence of such polynucleotides from individuals displaying symptoms of Type II diabetes can be determined and compared with sequences from individuals not displaying these symptoms.

Direct cDNA selection can be used to isolate segments of expressed DNA from a region on chromosome 20q between D20S195 and D20S119, using primer walking, as described above, or any other method. M. Lovett, J. Kere, L. M. Hinton, *Proc. Natl. Acad. Sci. USA* 88 9628–9632 (1991); and Jou et al. *Genomics* 24:410–413 (1994). By using bacterial artificial chromosomes (BAC) (e.g., commercially available from Research Genetics Inc., Huntsville, Ala.), a group of cDNAs can be identified, and hybridization and PCR-amplification (or other techniques for amplifying a polynucleotide) experiments can be used to determine if these cDNA segments are derived from the interval.

The cDNAs can then be used to determine whether specific sequences are differentially expressed in affected individuals compared to non-carrier individuals. For this purpose, cell lines can be generated from lymphoid cells isolated from an individual. Measurement of mRNA levels in lymphoblastoid cell lines can be used as an initial screen. The cell lines can be prepared by drawing blood from individuals, transforming the lymphoblasts with EBV and growing the immortalized cells in culture, using known techniques. Total RNA and DNA are extracted from the cultured human lymphoblastoid cell lines. Northern blot hybridization can be used to determine reduced levels of a specific sequence compared to levels from an unaffected, non-carrier individual as a result of mutations in the Type II diabetes gene on the chromosomes from these affected individuals which results in decreased levels of mature mRNA and play a primary role in Type II diabetes. Thus, alterations in gene sequences in affected individuals can be determined.

Any known technique can be used to amplify the polynucleotide comprising the gene(s) associated with Type II diabetes. These include polymerase chain reaction techniques. A polymerase chain reaction (PCR) can be used to amplify the gene and to determine its sequence from affected individuals. Sequence comparison with unaffected, non-carrier individuals can be carried out to identify polymorphisms in the gene sequence(s) that are associated with Type II diabetes.

The identification of the biochemical defect(s) that causes Type II diabetes could provide a basis for treatments for this disease. In addition, knowledge that certain mutations in the gene(s) are responsible for the disease allows mutation detection tests to be used as a definitive diagnosis for Type II diabetes.

Thus, the present invention provides an isolated polynucleotide that can be used in the identification of the presence (or absence) of a polymorphism in a Type II diabetes gene in a human and thus can be used in the diagnosis of Type II diabetes or in the genetic counseling of individuals, for example, those with a family history of Type II diabetes (although the general population can be screened as well). In particular, it should be noted that any mutation in a Type II diabetes gene away from the normal gene sequence is an indication of a potential genetic flaw; even so-called "silent" mutations that do not encode a different amino acid at the location of the mutation are potential disease mutations, since such mutations can introduce into (or remove from) the gene an untranslated genetic signal that interferes with the transcription and/or translation of the gene and/or processing of the mRNA. Thus, advice can be given to a patient concerning the potential for transmission of Type II diabetes if any mutation is present. While an offspring with the mutation in question may or may not have symptoms of Type II diabetes, patient care and monitoring can be selected that will be appropriate for the potential presence of the disease; such additional care and/or monitoring can be eliminated (along with the concurrent costs) if there are no differences from the normal gene sequence. As additional information (if any) becomes available (e.g., that a given silent mutation or conservative replacement mutation does or does not result in Type II diabetes), the advice given for a particular mutation may change. However, the change in advice given does not alter the initial determination of the presence or absence of mutations in the gene causing Type II diabetes.

Generally, mutations are identified in the human gene(s) for use in a method of detecting the presence of a genetic defect that causes or may cause Type II diabetes, or that can or may transmit Type II diabetes to an offspring of the human. Initially, the practitioner will be looking simply for differences from the sequence identified as being normal and not associated with disease, since any deviation from this sequence has the potential of causing disease, which is a sufficient basis for initial diagnosis, particularly if the different (but still unconfirmed) gene is found in a person with a family history of Type II diabetes. As specific mutations are identified as being positively correlated with Type II diabetes (or its absence), practitioners will in some cases focus on identifying one or more specific mutations of the gene that changes the sequence of a protein product of the gene or that results in the gene not being transcribed or translated. However, simple identification of the presence or absence of any mutation in the gene of a patient will continue to be a viable part of genetic analysis for diagnosis, therapy and counseling.

The actual technique used to identify the gene or gene mutant is not itself part of the practice of the invention. Any of the many techniques to identify gene mutations, such as direct sequencing of the gene from affected individuals, hybridization with specific probes, which includes the technique known as allele-specific oligonucleotide hybridization, either without amplification or after amplification of the region being detected, such as by PCR. Other analysis techniques include single-strand conformation polymorphism (SSCP), restriction fragment length polymorphism (RFLP), enzymatic mismatch cleavage techniques and transcription/translation analysis. All of these techniques are described in a number of patents and other publications, including, for example, "Laboratory Methods for Detection of Mutations and Polymorphisms in DNA" (1997) CRC Press, G. R. Taylor, ed.

Depending on the patient being tested, different identification techniques can be selected to achieve particularly advantageous results. For example, for a group of patients known to be associated with particular mutations of the gene, oligonucleotide ligation assays, "mini-sequencing" or allele-specific oligonucleotide (ASO) hybridization can be used. For screening of individuals who are not known to be associated with a particular mutation, single-strand conformation polymorphism, total sequencing of genetic and/or cDNA and comparison with standard sequences are preferred.

In many identification techniques, some amplification of the host genomic DNA (or of messenger RNA) will take place to provide for greater sensitivity of analysis. In such cases it is not necessary to amplify the entire gene, merely the part of the gene or the specific location within the gene that is being detected. Thus, the method of the invention generally comprises amplification (such as via PCR) of at least a segment of the gene, with the segment being selected for the particular analysis being conducted by the diagnostician.

Portions of the interval can be cloned into vectors, for example phage or plasmid vectors. Such vectors can be used to identify candidate cDNAs for screening for mutations in the DNA of Type II diabetes patients.

The candidate cDNAs can be subsequently screened for mutations in DNA from Type II diabetes patients. From the minimal candidate region defined by genetic mapping experiments a segment is left that is sufficiently large to contain multiple different genes.

Coding sequences from the surrounding DNA can be identified, and these sequences can be screened until a probable candidate cDNA are found. Candidates may also be identified by scanning databases consisting of partially sequenced cDNAs, known as expressed sequence tags, or ESTs. The database can be used to identify all cDNAs that map to the minimal candidate region for Type II diabetes. These cDNAs can then be used as probes to hybridize to the PI contig, and new microsatellites are isolated, which are used to genotype the "LD" sample. Maximal linkage disequilibrium in the vicinity of one or two cDNAs is identified.

Coding sequences can also be identified by exon amplification. Exon amplification targets exons in genomic DNA by identifying the consensus splice sequences that flank exon-intron boundaries. Briefly, exons are trapped in the process of cloning genomic DNA into an expression vector. These clones are transfected into COS cells, RT-PCR is performed on total or cytoplasmic RNA isolated from the COS cells using primers that are complementary to the splicing vector. Exon amplification can be performed using any known method. Another widely used approach is direct selection, which involves screening cDNAs using large insert clone contigs, with several steps to maximize the efficiency of hybridization and recovery of the appropriate hybrid.

Once cDNAs are identified, the most plausible candidates can be screened by direct sequencing, SSCP or using chemical cleavage assays.

Genetic and physical data can be used to map a Type II diabetes gene to a less than 6 cM region of chromosome 20q between D20S195 and D20S119. New markers from this region can be tested in order to locate a Type II diabetes gene in a region small enough to provide higher quality genetic tests for Type II diabetes, and to find the mutated gene(s). Narrowing down the region in which the gene is located will lead to sequencing of a Type II diabetes gene as well as cloning thereof. Further genetic analysis employing, for example, new polymorphisms flanking D20S195 and D20S119 as well as the use of cosmids, yeast artificial chromosome (YAC) clones, or mixtures thereof, are employed in the narrowing down process. The next step in narrowing down the candidate region can include cloning of the chromosomal region 20q including proximal and distal markers in a contig formed by overlapping cosmids and YACS. Subsequent subcloning in cosmids, BACs, YACs, plasmids, phages, or other vectors can generate additional probes for more detailed mapping.

Functional assays can also be applied to determine whether a given polynucleotide comprises a Type II diabetes gene. For example, a polynucleotide of the invention and/or a vector of the invention can be introduced into a mammalian cell which lacks a region on chromosome 20q between D20S195 and D20S119. A vector of the invention which comprises a polynucleotide comprising a region on chromosome 20q between D20S195 and D20S119 can be introduced into the cell by any known method. Thereafter, a functional assay such as the above-described glucose uptake assay can be used to determine whether the polynucleotide comprises a gene encoding a polypeptide involved with glucose uptake. In this case, a polynucleotide of the invention would be derived from a normal individual. If a the transformed cell contains a region on chromosome 20q between D20S195 and D20S119, derived from a normal individual, that is involved with glucose metabolism, then insulin-stimulated glucose uptake will be significantly above background for the cell. Background levels are established by performing a glucose uptake test on the untransformed cell which lacks a region on chromosome 20q between D20S195 and D20S119. Vectors comprising portions of the region on chromosome 20q between D20S195 and D20S119 from a normal individual can be generated and these vectors tested in the manner described above until the smallest fragment of the region is identified which results in the transformed cell having insulin-stimulated glucose uptake levels significantly above background levels. "Significantly above background levels" indicates that glucose uptake is at least about 20%, more preferably at least about 30%, more preferably at least about 40%, even more preferably at least about 50% or more, over glucose uptake levels of the untransformed cell, i.e., the cell which lacks a region on chromosome 20q between D20S195 and D20S119.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Pedigree Analyses

The study population that we have identified for mapping Type II diabetes genes, a founder population in the Bahamas, is ideal for population-based disease gene mapping. We have adopted several theoretical principles in carrying out the studies described herein, including those previously described. Freimer et al. (1996) *Amer. J. of Med. Genetics* 67:254–63; and PCT Publication No. WO 98/07887.

We have identified a model population with a diabetogenic pattern of body fat distribution and increased prevalence of adult onset diabetes (Type II). The study population is Caucasian and is genetically and environmentally homogeneous. We first explored the utility of such a population for a diabetes study because we identified several extremely large and genetically informative diabetes pedigrees. FIG. 1 shows a pedigree analysis of families belonging to this population. We soon discovered that this population is ideally suited for genetic mapping because this population is genetically homogeneous, having expanded rapidly from a small number of founders. Geographically, the study population is particularly isolated. Scheduled ferry service to the islands did not exist two decades ago and is now only available on a limited basis. Such limited access and the lack of hotels and restaurants to support tourism have contributed to a continued history of genetic isolation for the population.

The founder population was derived primarily from 70 founders of English ancestry whose ship wrecked on the uninhabited islands in the 17th century, and the introduction a century later of a small number of Tory Loyalists, also of English ancestry. In the latter part of the 18th Century, a descendant of the original founding population and the daughter of a Tory Loyalist founded the principal island population to be used for our study. They had thirteen children and the population expanded rapidly due to a continued history of large sibships. Because of the "isolationist" nature of this community, the population has remained genetically isolated. We located a 700-member pedigree for the population on the primary study island. The current estimate of the number of descendants still remaining in the more isolated sections of the Bahamas is on the order of 4,000 people. Pedigree analysis is shown in FIG. 1.

The power to detect disease genes can be investigated by simulating linkage using any known method, including, but not limited to, TDT and Terwilliger. Specifications involved in disease transmission are not necessary for these methods. Based on our preliminary findings, our population exhibits a similar expansion to that of the Costa Rican founder population previously described (WO 98/07887). It is assumed that the affected individuals in the Costa Rican population are on average 12 generations removed from a common ancestor who transmitted the disease allele/s. A second population in which affected individuals are approximately 15 generations removed from a common ancestor who transmitted the disease allele/s was included in the analysis. We estimate, based on our preliminary findings, that the Bahamian population will fall near this threshold. It was estimated that the Bahamian population has a similar degree of relatedness. These tests were compared under several scenarios, varying the genetic model for disease transmission and the size of the study sample.

Genealogical screening was conducted to establish the place of origin of each subject's family, back to the great-grandparental generation. This protocol was based on the assumption that those individuals whose great-grandparents' surnames match the original 70 founders or Tory Loyalist families, are likely to be descended from the founder population established in the 17th and 18th Centuries. There has been little new immigration into these remote communities/islands. A subject was included in the study if at least five of his/her eight great-grandparents were born in the islands. Of the subjects who have been interviewed, we have completed the genealogical assessment for 50 community residents. Of these, 20 subjects have been diagnosed with diabetes.

Clinical Presentation of Subject Population

The first study subjects to be recruited were identified during a diabetes health fair which our study group hosted on the island in 1996. Anthropometric measurements were assessed and estimates were made of central fat levels in this genetically isolated population. Intra-abdominal adipose tissue (IAAT) levels were significantly greater in the Bahamian founder population than for Caucasian, age-matched controls measured in Birmingham (p=0.0001). A series of anthropometric and skinfold measurements were assessed and used to estimate the levels of IAAT. Prediction equations for estimating the levels of IAAT have been described. Kekes-Szabo, T., et al. (1996) *Intl. J. of Obesity & Related Metabolic Disorders* 20(8):753–8; and Kekes-Szabo, T. (1994) *Obesity Res.* 2(5):450–457. Kekes-Szabo, T., et al. (1996) *Intl. J. of Obesity & Related Metabolic Disorders* 20(8):753–8; and Kekes-Szabo, T. (1994) *Obesity Res.* 2(5) :450–457. The prediction equation for estimating the levels of IAAT used in these studies was as follows:

(2.57×umbilicus circumference+0.92×age+0.69×suprailiac skinfold)−188.61

The diabetes in our study population is characteristic of Type II diabetes seen in other Caucasian populations: central obesity-associated diabetes mellitus with an adult age of onset and no initial requirement for insulin. Clinical characteristics of individuals examined are shown in Table 1. Values are given as mean±standard deviation.

TABLE 1

| Clinical characteristic | Non-diabetic | Diabetic |
| --- | --- | --- |
| n | 8 | 8 |
| % male | 25 | 25 |
| Current age (years) | 61 ± 11 | 62 ± 11 |
| Current BMI (kg/m$^2$) | 23 ± 4 | 37 ± 12 |
| Fasting Blood Glucose (mg/dL) | 97 ± 10 | 197 ± 66 |
| Blood Pressure (mmHg) | 131/80 ± 12/10 | 147/87 ± 21/5 |
| Cholesterol (mg/dL) | 226 ± 37 | 260 ± 56 |
| Triglycerides (mg/dL) | 143 ± 88 | 222 ± 100 |
| Average age at diagnosis (years) | — | 53 ± 10 |

The diabetes in the individuals studied resembles neither MODY nor Type I diabetes.

In concordance with our observations of elevated levels of IAAT, many of the Bahamian subjects who participated in the health fair reported a strong family history of diabetes. Subjects have been assessed for diabetes either through medical records (fasting glucose or oral glucose tolerance test (OGTT)) or assessed at one of our health fairs (fasting glucose), in accordance with the published guidelines of the American Diabetes Association.

Example 2

Linkage Disequilibrium Analysis

The microsatellite marker set that is used for the random, whole genome screen is the ABI Prism Linkage Mapping Set Version 2 (Applied Biosystems, Inc./Perkin Elmer, Foster City, Calif.). This Mapping Set consists of 400 fluorescent-labeled PCR primer pairs that define a 10-cM resolution linkage map, as shown in FIGS. 3A and 3B.

The primers are selected to amplify microsatellite loci selected from the Genethon human linkage map. Weissenbach et al. (1992); Weber et al. (1993). The set is divided into 28 panels, each containing 10 to 20 PCR primer pairs. Each of the primer pairs has been optimized for accuracy and is labeled with one of three dyes. During each run, a CEPH (Centre d'etude du polymorphisme humain; a collaborative genetic mapping of the human genome) standard control DNA sample is included as a size reference for each marker tested. For each marker tested, CEPH individuals 1331-01, 1331-02, and 1347-02 are used as size standards. CEPH DNAs are obtained from the NIGMS Human Genetic Mutant Cell Repository Coriell Institute for Medical Research (Camden, N.J.).

Each sample is co-electrophoresed with an internal size standard. The Genescan 400HD ROXI size standards are an improved size standard for the ABI instrument. The size standard includes 21 evenly spaced fragments labeled with ROX. Because it is labeled with a different color dye than the samples, the size standard can be included with each sample. Any sample which did not meet stringent criteria for size calling (for example, peak heights must be greater than 100 to avoid possible miscalling of a homozygote) is repeated.

One advantage of automated genotyping (utilizing fluorescent dyes and including size standards in each run) compared to manual genotyping (utilizing isotopic labeling and size standards run in adjacent lanes), is that genome screens can proceed before the entire sample is collected. The ABI Prism Linkage Mapping Set Version 2 is designed to maximize the efficiency of typing multiple markers in a single run; once the markers are labeled with fluorescent dye they can be used at any time over the course of the project. Once the samples are amplified, they can be stored over time and run at a later date. Thus, it is straightforward to continually screen the genome, as new samples are completed.

Individuals are genotyped using highly polymorphic microsatellite markers spaced across the genome with 10 cM resolution, followed by a screen using more densely spaced markers (i.e., about 800–1000 markers resulting in a map with 3–5 cM resolution). Denser maps of markers can be used, as they become available, to localize more accurately a locus (loci) associated with Type II diabetes.

Genome screening results can be analyzed using any known method for detecting association between diabetes and marker loci, including, but not limited to, transmission disequilibrium tests: 1) TDT, Spielman, R. S. et al. (1992) *Nature Genetics* 1(2):82–3); 2) and the linkage disequilibrium analysis of Terwilliger (Terwilliger, J. (1995) *Amer. J. of Human Genetics* 56(3):777–787). Based on computer simulations, we had a high probability of detecting diabetes loci with these samples, even if diabetes is highly etiologically heterogeneous in the population. We used an inclusive threshold for identifying regions associated with Type II diabetes, namely a p-value (in any of the three tests) of 0.05.

Analysis of Chromosome 20 Markers

The Type II diabetes Linkage Analysis Consortium has provided a framework of 10 markers on chromosome 20 for initial analysis. The markers which were used to type DNAs from individuals in our Bahamian population are shown in Table 2.

TABLE 2

| Marker | GenBank Accession No. |
|--------|----------------------|
| D20S186 | Z23375 |
| D20S112 | Z16842 |
| D20S195 | Z24371 |
| D20S107 | Z16656 |
| D20S119 | Z17198 |
| D20S178 | Z23757 |
| D20S100 | Z16487 |
| D20S171 | Z23313 |

Due to the growing consensus for linkage to diabetes on chromosome 20q (Ji, L., et al. (1997) *Diabetes* 46(5):876–81; Bowden, D. W., et al. (1997) *Diabetes* 46(5):882–86; Velho, G., et al. (1997) *Diabetes and Metabolism* 23(Suppl. 2):34–37; www.sph.umich.edu/group/statgen/consortium), we used the chromosome 20 markers shown in Table 2 to test DNA samples from affected individuals from our pedigree family (FIG. 1) as well as from seven distantly-related, affected individuals. "Affected" individuals are those diagnosed with Type II diabetes. The set of markers shown in Table 2 covers a region of 69.3 cM on chromosome 20.

Blood samples were obtained from each individual tested, and DNA was isolated from the samples using standard techniques. DNA samples from affected individuals in the pedigree, as well as distantly related, affected individuals, were tested by PCR.

PCR reactions were conducted using the following protocol. The reaction mixture contained 1.0 $\mu$l primer mix (5 $\mu$M each primer), 1.2 $\mu$l DNA template (50 ng/il), 9.0 $\mu$l True Allele PCR Premix, and 3.8 $\mu$l sterile deionized water. True Allele PCR Premix (Perkin Elmer/ABI) contains PCR Buffer II, GeneAmp deoxynucleotide mix, AmpliTaq Gold DNA polymerase and $MgCl_2$. For each microsatellite marker-specific primer pair, one member of each pair was labelled with a fluorescent dye. In addition to the primer pairs specific to each chromosome 20 marker tested, size standard primer pairs and corresponding template were included. The Genescan 400HD ROXI size standards are an improved size standard for the ABI instrument used in our studies. The size standard includes 21 evenly spaced fragments labeled with ROX, a red fluorescent dye. Each sample was subjected to capillary electrophoresis using an ABI310 Genetic Analyzer (Perkin Elmer/ABI, Foster City, Calif.) automated sequencing instrument. Since PCR reactions for each microsatellite marker included size standard control PCR reactions, each sample is co-electrophoresed with an internal size standard. The instrument then calculates, based on the size standard, the size of the fragments amplified with microsatellite marker-specific PCR primers. "Shared alleles" are identified as microsatellite marker-specific PCR fragments which are identical in size between and/or among individuals tested.

Figure 2:
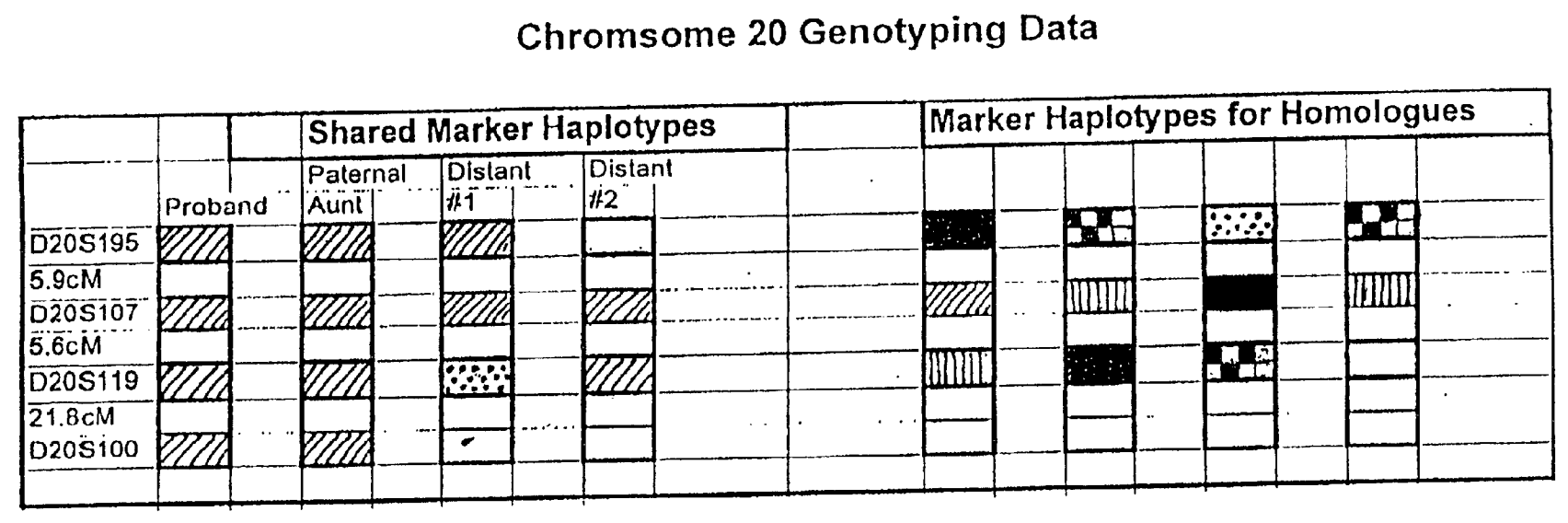

Six of these seven subjects shared a common allele with an affected individual in the pedigree for an anonymous marker located at chromosome 20q12–13; four of these share an ancestral haplotype which extends greater than 10 cM, as shown in FIG. 2.

The one subject who does not share alleles at this 10 cM region is assumed to be a phenocopy.

The marker D20S107 demonstrated a higher than expected allele sharing among the affecteds. In order to assign a set of alleles to each copy of chromosome 20, an additional marker set, containing markers close to D20S107, were used to test the DNAs from the same panel of pedigree members. The additional markers used were D20S477, D20S478, D20S170, and D20S481 (GenBank Accession Numbers G08047, G08048, Z23468, and G08051, respectively). Using these markers, a haplotype was generated.

Once the haplotyping was complete, closely spaced markers that surround D20S107 were used for Terwilliger linkage disequilibrium analysis. These markers are shown in Table 3.

TABLE 3

| Marker | Sequence ID |
|--------|-------------|
| D20S195 | SEQ ID NO:1 |
| D20S107 | SEQ ID NO:3 |
| D20S170 | SEQ ID NO:4 |
| D20S119 | SEQ ID NO:2 |

These markers cover an 11.4 cM region on chromosome 20. The maximum LOD score was found between D20S107 and D20S170. The interval between D20S107 and D20S170 is 1.2 cM. Thus, it appears that a locus associated with Type II diabetes is in the vicinity of D20S107.

Using this method, we localized the interval to a small region between D20S195 and D20S119, most likely close to D20S107. We did not detect the HNF-4α V3931 mutation.

Example 3

Polymorphisms in a Cis Region of the KRML Gene Associate with Type II Diabetes

Protocol for the SNP typing

The polymerase chain reaction conditions were as follows. PCR rxn: DNA 100 ng; 10×Buffer (100 mM Tris, pH 8.3; 500 mM KCl) 5 µl; 25 mM dNTPs 4 µl; 25 mM MgCl$_2$ 3 µl; Forward Primer (10 µM) 2 µl; Reverse Primer (10 µM) 2 µl; Taq polymerase (5U/µl) 0.2 µl; volume total 50 µl. PCR parameters were as follows: 95° C. 3 minutes to denature the template; followed by 35 cycles of: 94° C. 1 minute; 55° C. 1 minute; and 72° C. 1.5 minute. Following the 35 cycles, the reaction was carried out further at 72° C. 10 minutes.

The PCR product was then sequenced by direct PCR sequencing in both directions, using the forward and reverse primers as follows.

Forward primer for SNP58: 5'-GTT TTC TTG GCT TTA GTC C-3' (SEQ ID NO:5)

Reverse primer for SNP 58: 5'-GAG ACC ATT ACT CAA AGT GG-3' (SEQ ID NO:6). The size of the resulting PCR fragment was 340 base pairs.

Results

Figure 4:
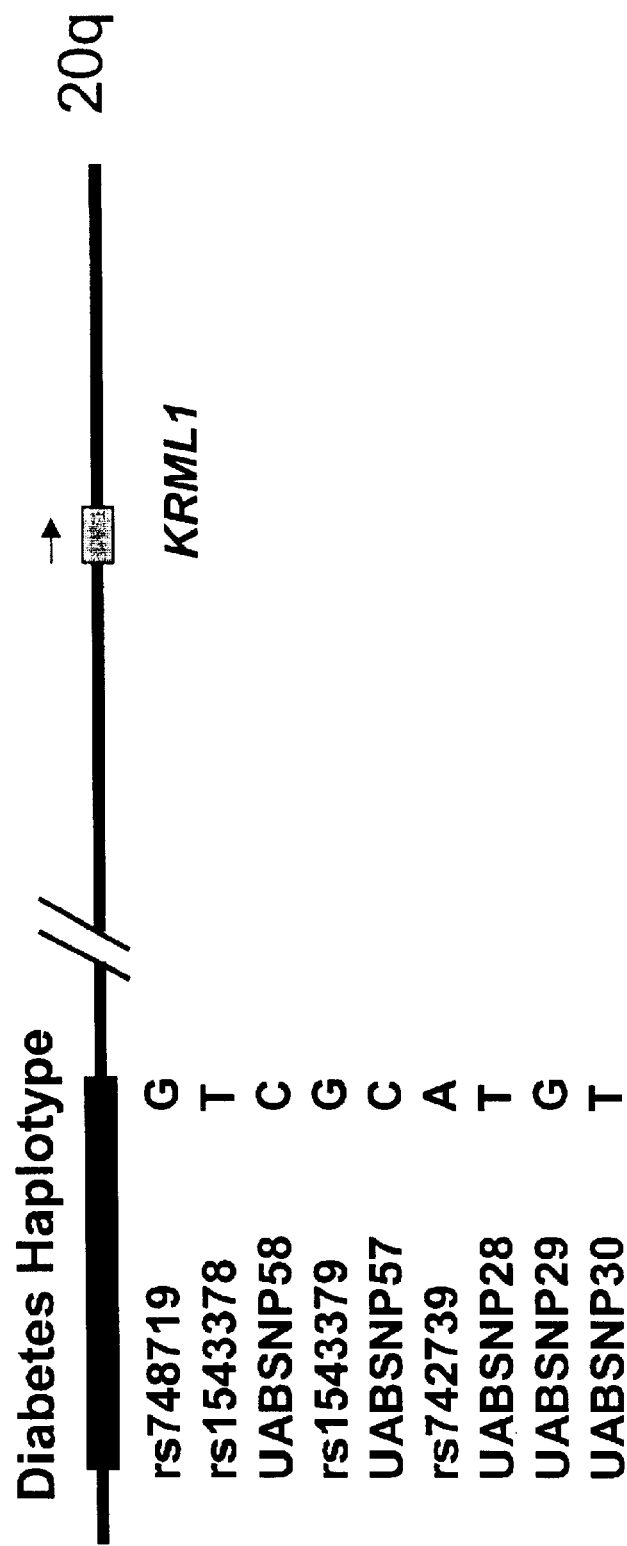
FIG. 4 shows several single nucleotide polymorphisms in a 5' flanking region of a KRML1 gene.

We carried out SNP genotyping of the sequences adjacent to the D20S107 marker. We analyzed a total of 52 SNP markers which span ~11 cM. Of these, 24 were heterozygous in the population. Of these, 9 form a diabetes haplotype (FIG. 4). The closest gene, KRML1, is a single exon gene located downstream of the haplotype.

One polymorphism in particular, UABSNP58, is highly represented in affecteds. This polymorphism is within the region between D20S195 and D20S119. UABSNP58 is present in affected individuals in the general population. The sequence of PCR fragment is shown in FIG. 5A (SEQ ID NO:7). The two sequences in parentheses are rs1543378 (also referred to as "SNP27"; where the polymorphism is an A to T substitution) and rs1543379 (also referred to as "SNP26"; where the polymorphism is an A to G substitution). The nucleotide in bold type is SNP58 (T to C substitution; where T is found in normal individuals, and C is found in individuals with Type II diabetes). FIG. 5B shows the same sequence, without SNP58, e.g., the sequence at SNP58 found in normal individuals.

The SNPs that are associated with Type II diabetes are located in a region that is syntenic to cis-acting elements of the KRML1 homologous mouse gene, MafB. Our results demonstrate that KRML is a diabetes susceptibility locus.

KRML is expressed in skeletal muscle and is a member of the MAF family of basic-leucine zipper (bZIP) transcription factors that participate in cellular differentiation. To determine the level of KRML expression in adipose tissue, compared to other tissues, including skeletal muscle tissue, we used a KRML nucleic acid as a probe to analyze RNA from various tissues. The data show that KRML is expressed at the highest levels in both skeletal muscle and adipose tissue. The tissue distribution and function of KRML1 are consistent with a role in diabetes susceptibility.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for detecting a predisposition of an individual to develop Type II diabetes, comprising analyzing a polynucleotide sample derived from the individual for the presence of a nucleotide sequence of SEQ ID NO:7, wherein the presence of a nucleotide sequence of SEQ ID NO:7 is indicative of a predisposition in the individual to develop Type II diabetes.

2. The method of claim 1, wherein said analyzing comprises contacting the polynucleotide sample with at least one probe for a sufficient amount of time to allow for specific hybridization of the sample polynucleotide to the probe under stringent hybridization conditions, wherein the probe comprises a nucleotide sequence of SEQ ID NO:7; and b) determining the presence of specific hybridization between the sample polynucleotide and the probe, wherein specific hybridization of the probe to the sample polynucleotide provides for the detection of the a nucleotide sequence of SEQ ID NO:7 in the individual.

3. The method of claim 1, wherein said analyzing comprising a) amplifying a portion of the polynucleotide sample that comprises a nucleotide sequence of SEQ ID NO:7 to generate an amplified nucleic acid product, wherein said amplification is carried out using a polymerase chain reaction and a pair isolated nucleic acid molecules, each from about 10 to 200 nucleotides in length, the first nucleic acid molecule of the pair comprising a sequence of at least 10 contiguous nucleotides having 100% sequence identity to the nucleotide sequence of SEQ ID NO:7 and the second nucleic acid molecule of the pair comprising a sequence of at least 10 contiguous nucleotides having 100% sequence identity to the reverse complement of the nucleotide sequence of SEQ ID NO:7, wherein the sequence of the second nucleic acid molecule is located 3' of the nucleic acid sequence of the first nucleic acid molecule in SEQ ID NO:7; and b) sequencing the amplified nucleic acid product.

4. The method of claim 3, wherein said first nucleic acid molecule comprises a nucleotide sequence of SEQ ID NO:5.

5. The method of claim 3, wherein said second nucleic acid molecule comprises a nucleotide sequence of SEQ ID NO:6.

* * * * *